US012409007B2

(12) United States Patent
Hollopeter et al.

(10) Patent No.: US 12,409,007 B2
(45) Date of Patent: Sep. 9, 2025

(54) STERILIZABLE COVER FOR HANDLE OF ACCESSORY OF MEDICAL SUSPENDED CEILING ASSEMBLY

(71) Applicant: American Sterilizer Company, Mentor, OH (US)

(72) Inventors: Michael Hollopeter, Kirtland, OH (US); David A. Westenfelder, II, Mantua, OH (US)

(73) Assignee: American Sterilizer Company, Mentor, OH (US)

( * ) Notice: Subject to any disclaimer, the term of this patent is extended or adjusted under 35 U.S.C. 154(b) by 146 days.

(21) Appl. No.: 18/143,194

(22) Filed: May 4, 2023

(65) Prior Publication Data

US 2023/0355343 A1 Nov. 9, 2023

Related U.S. Application Data

(60) Provisional application No. 63/338,070, filed on May 4, 2022.

(51) Int. Cl.
*A61B 50/00* (2016.01)
(52) U.S. Cl.
CPC .................................... *A61B 50/00* (2016.02)
(58) Field of Classification Search
CPC ............. A61B 50/00; A61B 2090/0813; Y10S 16/906; Y10S 16/12
See application file for complete search history.

(56) References Cited

U.S. PATENT DOCUMENTS 3,066,362 A * 12/1962 Merrigan ................... A61L 2/26
422/310
4,559,671 A * 12/1985 Andrews ................ A61B 46/10
16/DIG. 19

(Continued)

FOREIGN PATENT DOCUMENTS

WO 9516875 A1 6/1995

OTHER PUBLICATIONS

Finite Element Modeling of Soft Fluidic Actuators: Overview and Recent Developments, Xavier, Advanced Intelligence Systems, Oct. 28, 2020 (2020).*

(Continued)

*Primary Examiner* — Jason W San
*Assistant Examiner* — Matthew J Sullivan
(74) *Attorney, Agent, or Firm* — Renner, Otto, Boisselle & Sklar, LLP

(57) ABSTRACT

A sterilizable cover for a handle of an accessory of a medical suspended ceiling assembly includes a generally tubular stem portion and an annular flange portion. The generally tubular stem portion has a sufficient size to be gripped by the human hand, and has a proximal end that is open and a distal end that is closed, and defines a cavity along a longitudinal axis for receipt therein of a handle grip portion. The generally tubular stem portion includes a friction fit portion that is configured to flex radially outwardly to create a friction fit with a portion of the handle grip portion upon receipt of the handle grip portion in the cavity of the generally tubular stem portion. The annular flange portion extends radially outwardly from a proximal end of the generally tubular stem portion. The generally tubular stem portion and the annular flange portion are a single continuous piece of flexible silicone rubber.

35 Claims, 13 Drawing Sheets

(56) References Cited

U.S. PATENT DOCUMENTS

| | | | | |
|---|---|---|---|---|
| 4,605,124 | A * | 8/1986 | Sandel | A61B 46/10 362/399 |
| 4,777,574 | A * | 10/1988 | Eisner | A61B 46/10 362/399 |
| 4,844,252 | A * | 7/1989 | Barron | F21V 21/403 362/804 |
| 4,975,826 | A * | 12/1990 | Bell | A61G 15/10 362/804 |
| 4,976,299 | A * | 12/1990 | Bickelman | A61B 46/10 362/804 |
| 5,065,296 | A * | 11/1991 | Cude | F21V 21/403 362/399 |
| 5,188,454 | A * | 2/1993 | Quintanilla | F21V 21/403 362/399 |
| 5,355,292 | A * | 10/1994 | Hoftman | A61B 46/10 362/400 |
| 5,465,461 | A * | 11/1995 | Sandel | B25G 1/02 16/421 |
| 5,469,600 | A * | 11/1995 | Sandel | A61B 46/10 362/399 |
| 5,709,465 | A * | 1/1998 | Lanzone | F21V 21/406 362/399 |
| 5,884,996 | A * | 3/1999 | Cottone | A61B 46/10 362/399 |
| 6,269,949 | B1 * | 8/2001 | Gottlieb | B65D 1/265 220/739 |
| 6,305,937 | B1 * | 10/2001 | Williams | A61C 3/00 433/116 |
| 6,390,818 | B2 * | 5/2002 | Ferranti | B25G 1/102 433/141 |
| 6,447,149 | B1 * | 9/2002 | Kaforey | A61B 46/10 362/399 |
| 6,692,141 | B2 * | 2/2004 | Jesurun | A61B 90/30 362/399 |
| 7,757,352 | B2 * | 7/2010 | Halamish | A61B 46/10 362/400 |
| 8,752,987 | B1 * | 6/2014 | Hoftman | A61B 46/10 362/399 |
| 8,789,243 | B2 * | 7/2014 | Denmark | F21V 21/403 362/399 |
| 10,321,970 | B1 * | 6/2019 | Hollopeter | A61B 90/30 |
| 10,439,611 | B2 * | 10/2019 | Alexanderson | H01H 19/04 |
| 10,605,443 | B2 * | 3/2020 | Kim | F21V 17/16 |
| 10,650,988 | B2 * | 5/2020 | Sanders | A61B 90/30 |
| D894,468 | S * | 8/2020 | Hollopeter | D26/113 |
| 10,987,188 | B2 * | 4/2021 | Betts | A61B 90/30 |
| 11,039,899 | B2 * | 6/2021 | Hollopeter | A61B 90/30 |
| 11,317,984 | B2 * | 5/2022 | Barten | A61B 46/10 |
| 11,484,382 | B2 * | 11/2022 | Hollopeter | A61B 90/36 |
| 11,950,937 | B2 * | 4/2024 | Chang | A61B 50/00 |
| 2003/0161158 | A1 * | 8/2003 | Jesurun | A61B 90/30 362/399 |
| 2006/0059663 | A1 * | 3/2006 | D'Ambrosio | E05B 1/0069 16/441 |
| 2014/0075721 | A1 | 3/2014 | Denmark | |
| 2017/0056120 | A1 * | 3/2017 | Benatav | A61B 46/10 |
| 2017/0254522 | A1 * | 9/2017 | Liang | F21V 23/0435 |
| 2020/0085524 | A1 * | 3/2020 | Ramadorai | A61B 90/08 |
| 2021/0307595 | A1 * | 10/2021 | Meah | A61B 1/0014 |
| 2023/0181279 | A1 * | 6/2023 | Kammer | A61B 46/10 220/315 |
| 2023/0355343 | A1 * | 11/2023 | Hollopeter | A61B 90/361 |

OTHER PUBLICATIONS

PCT/US2023/020936; PCT International Search Report and Written Opinion of the International Searching Authority mailed Jul. 28, 2023.

* cited by examiner

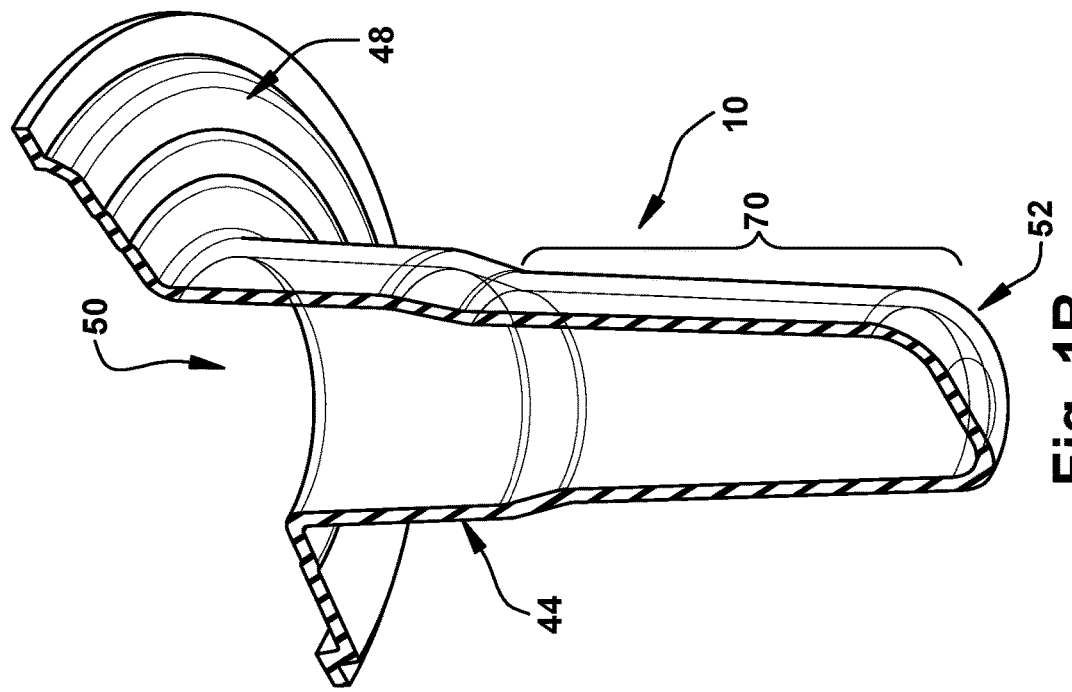
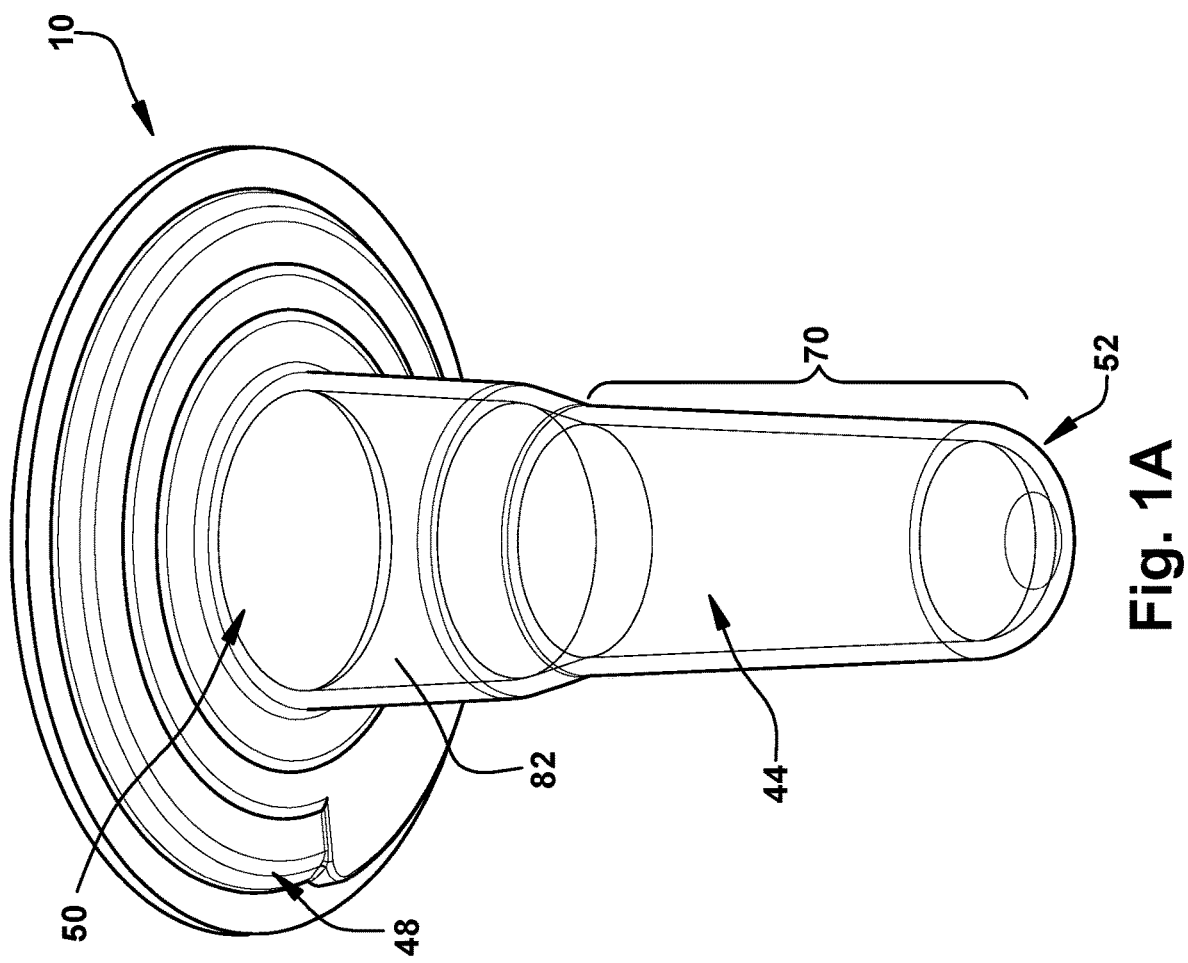

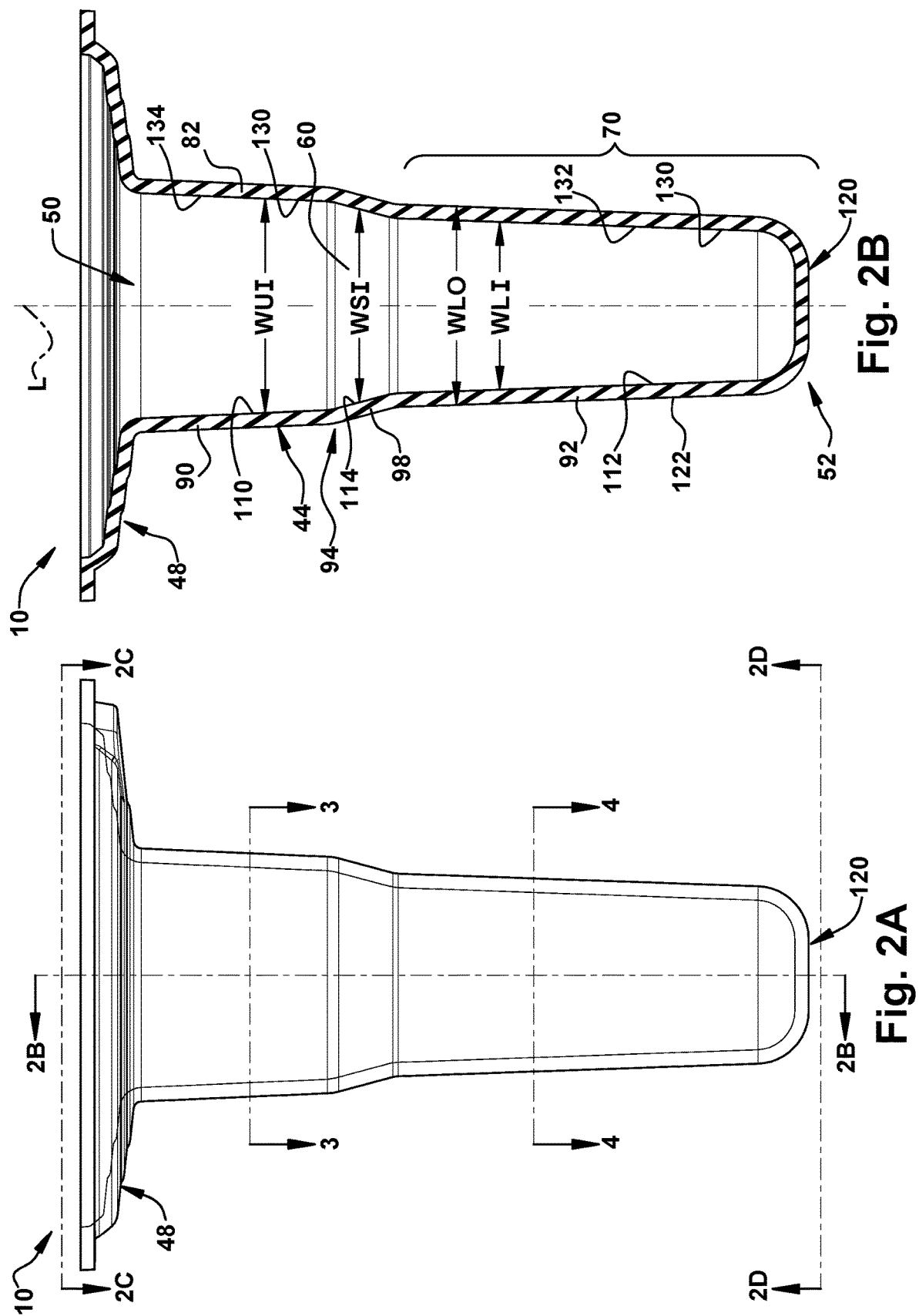

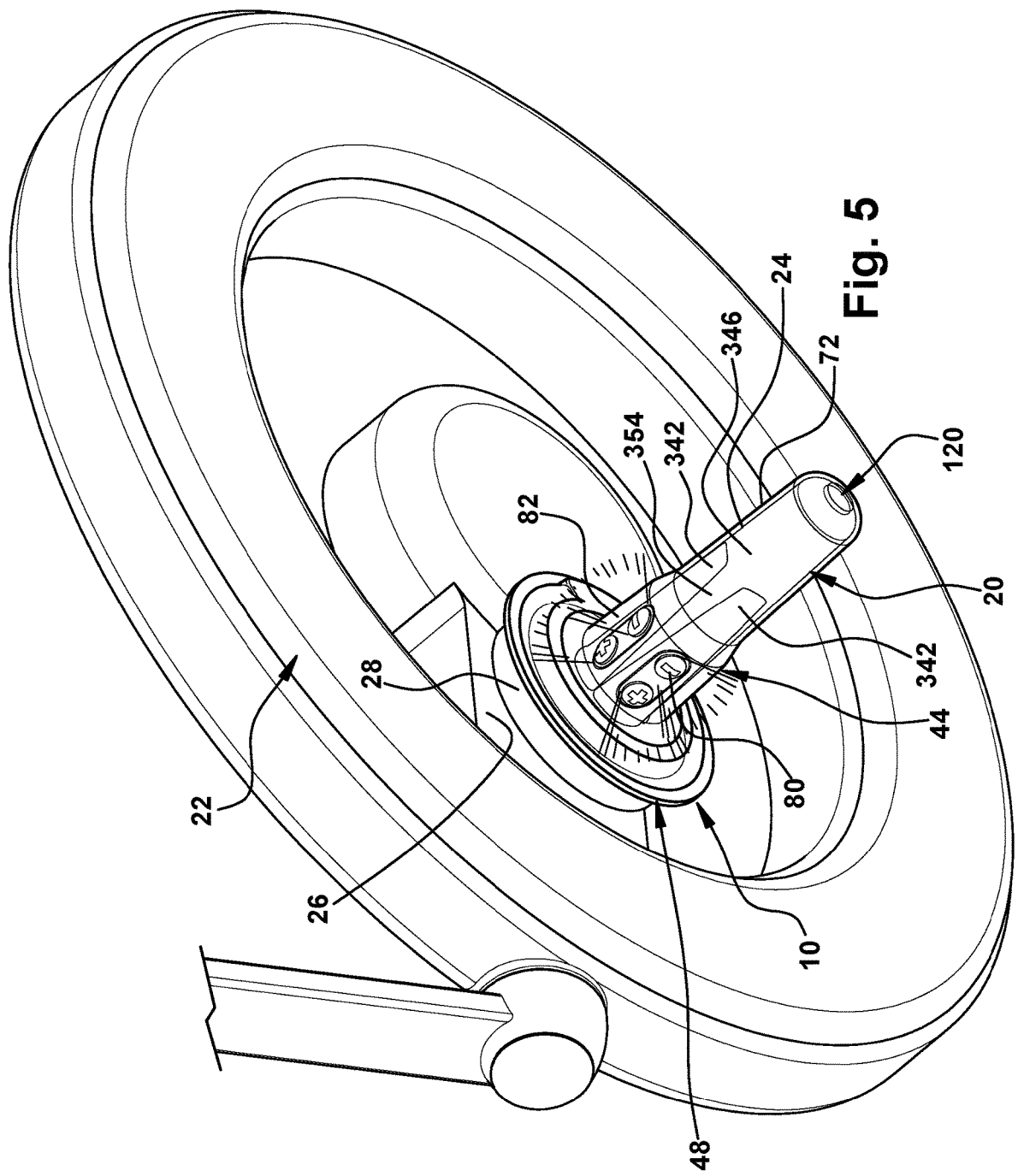

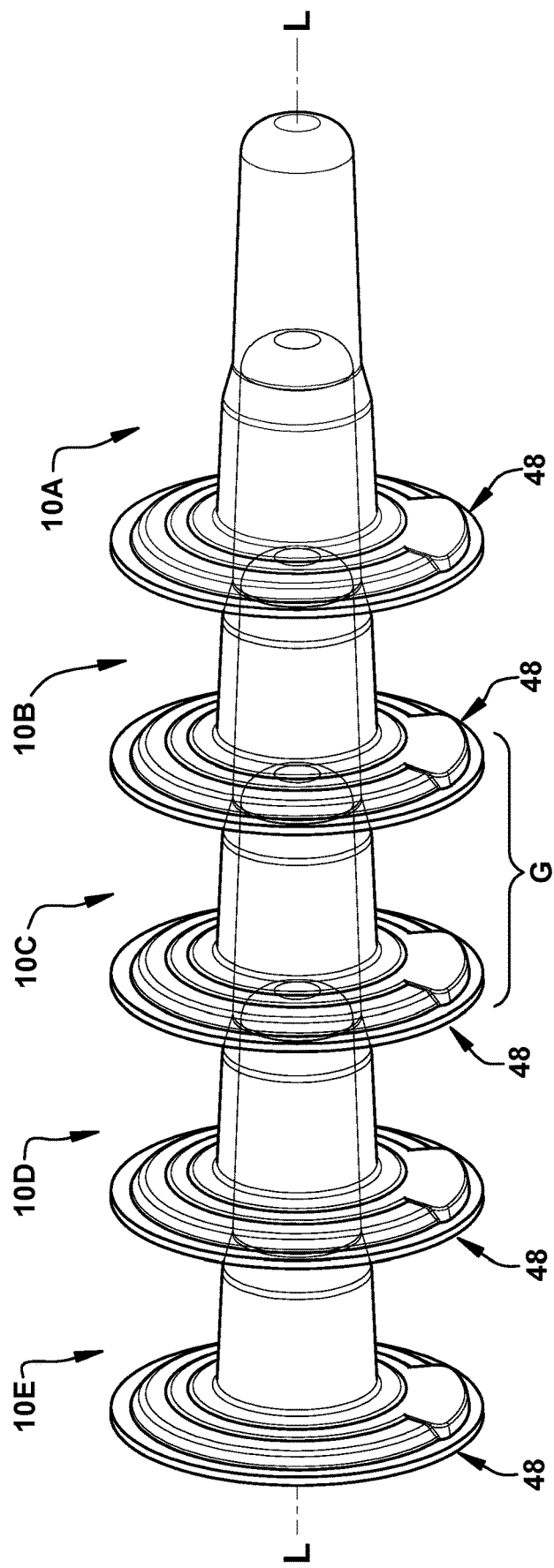

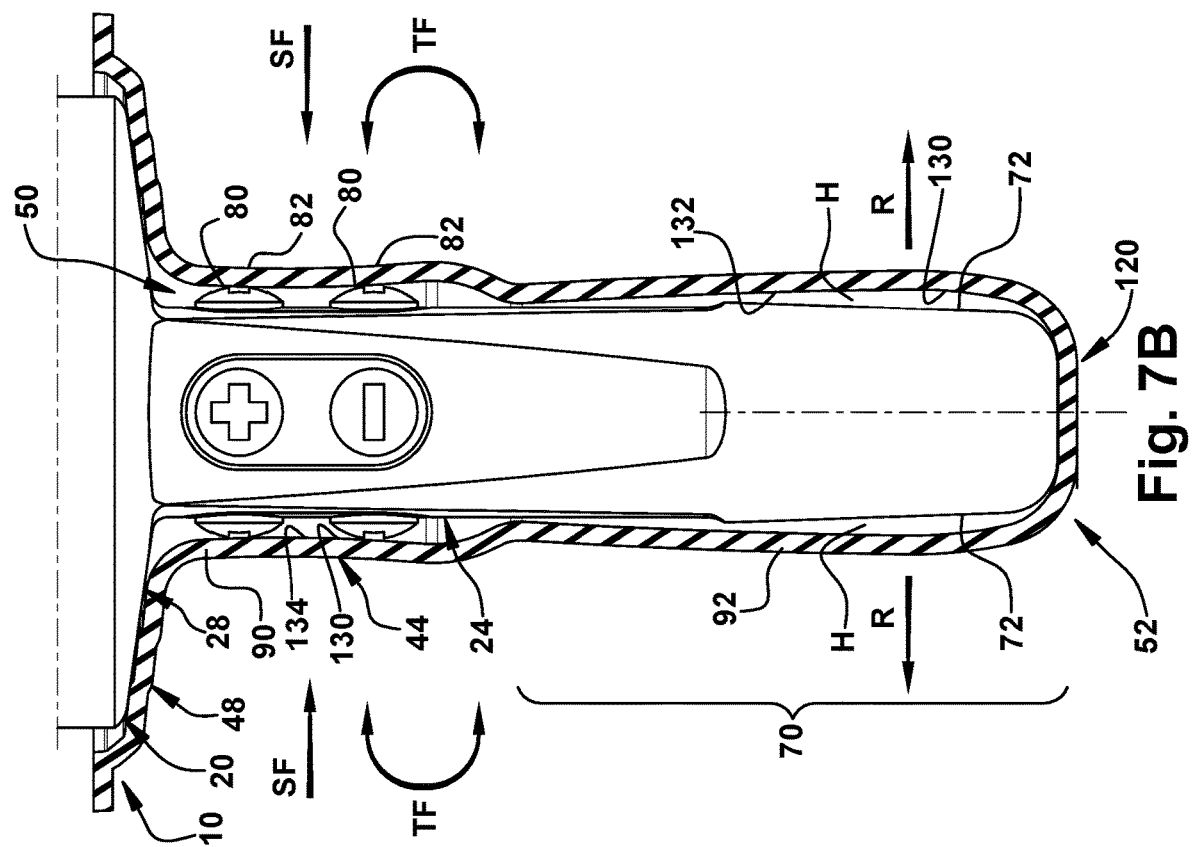
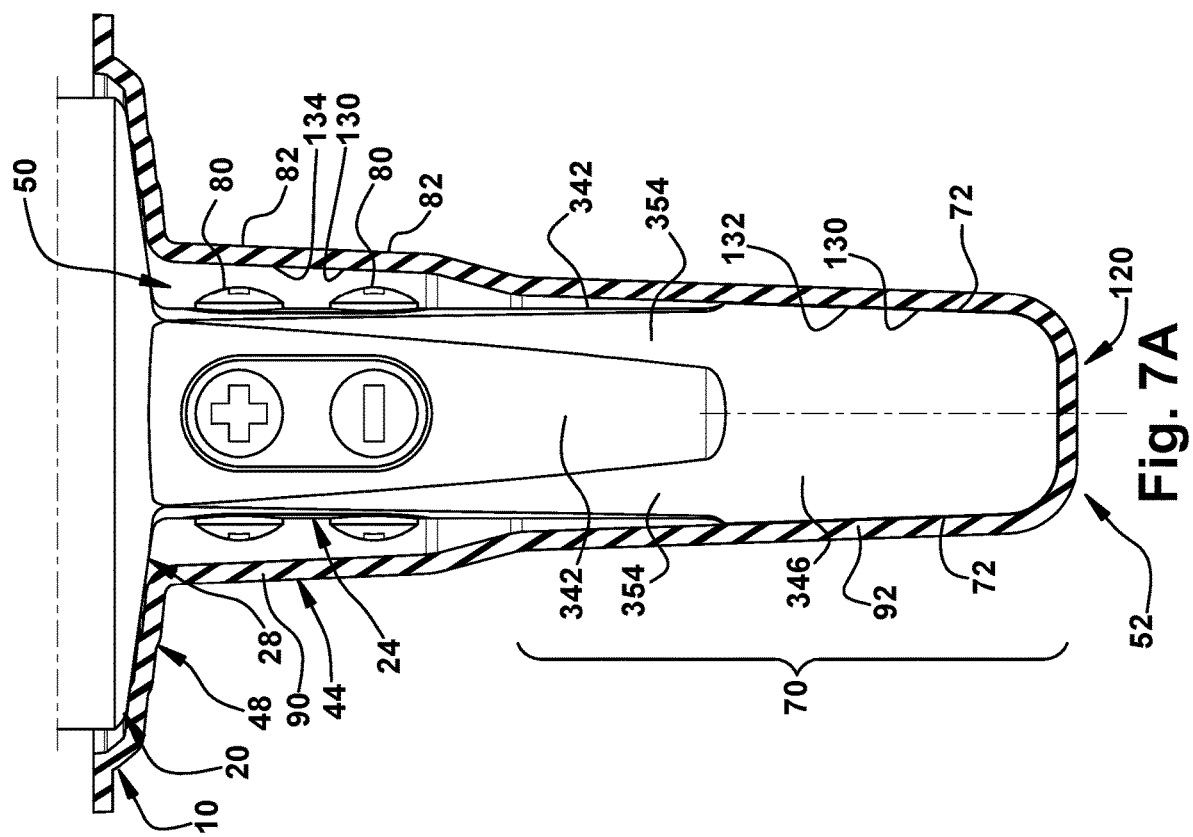

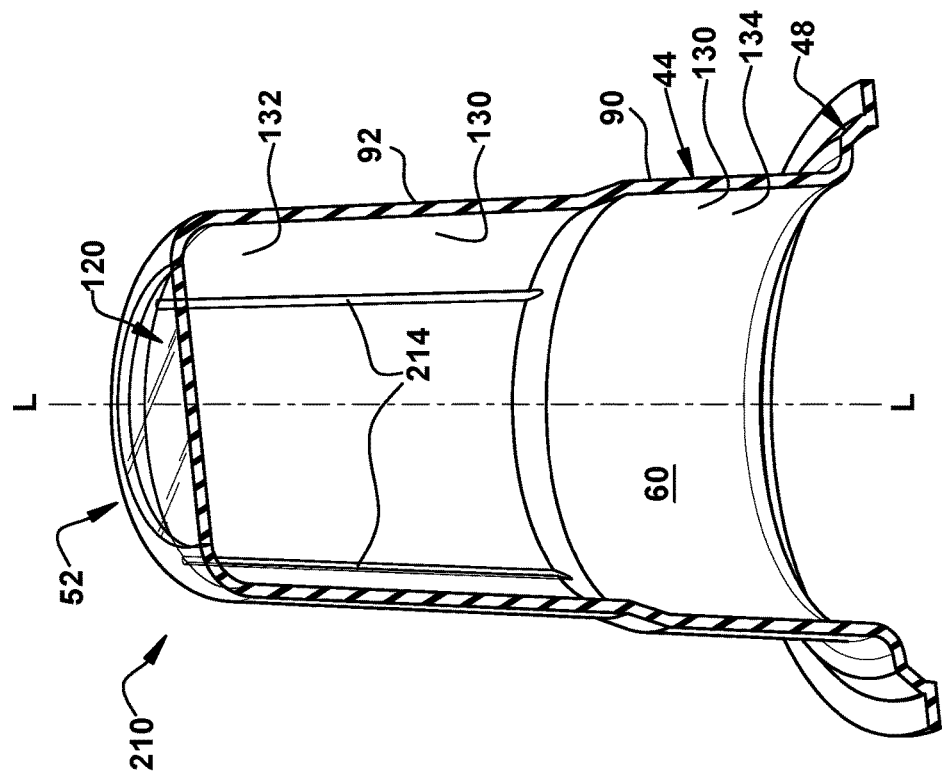
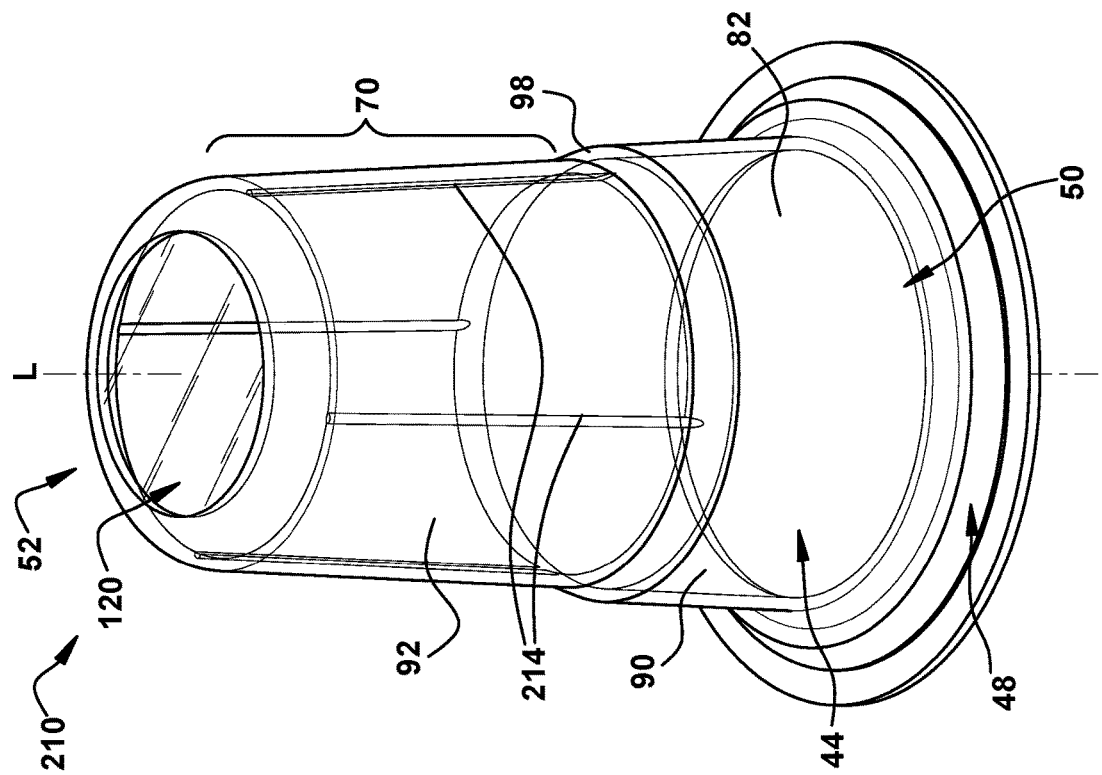

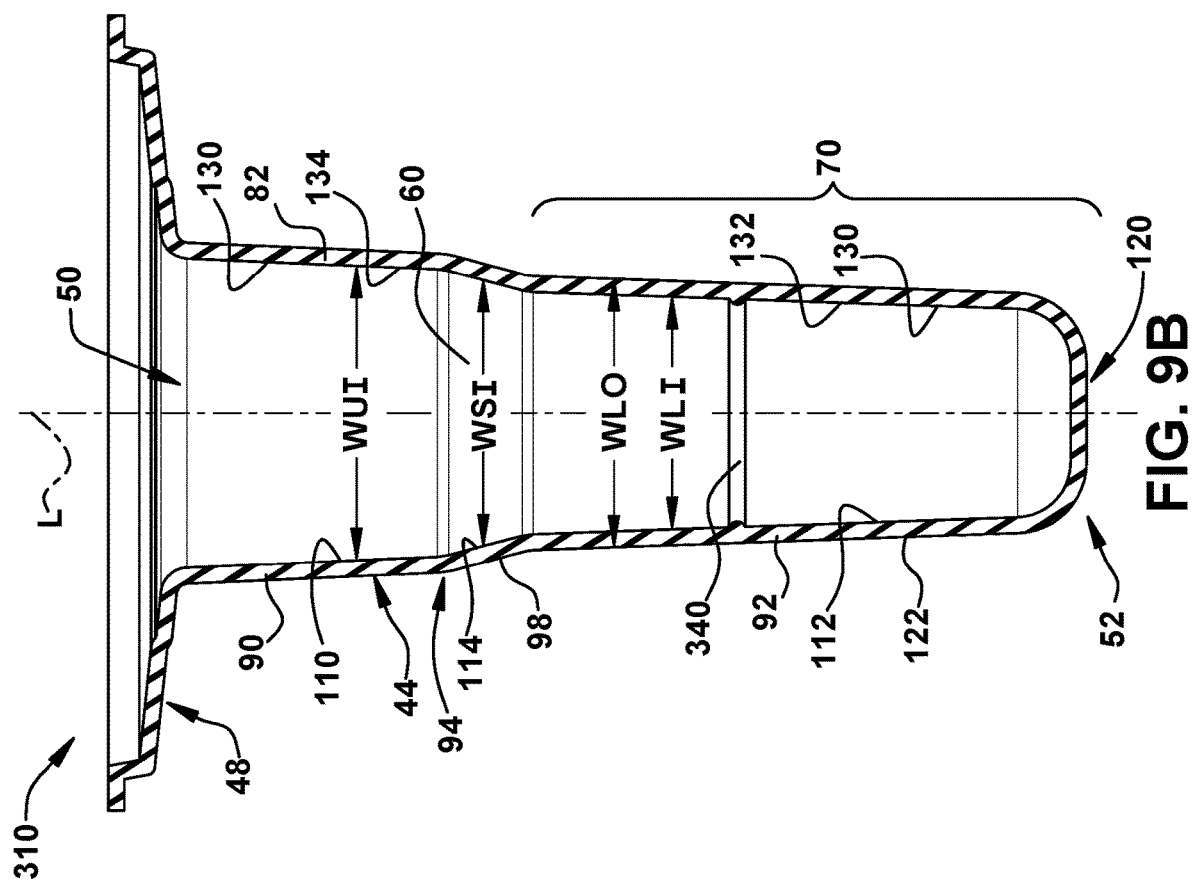
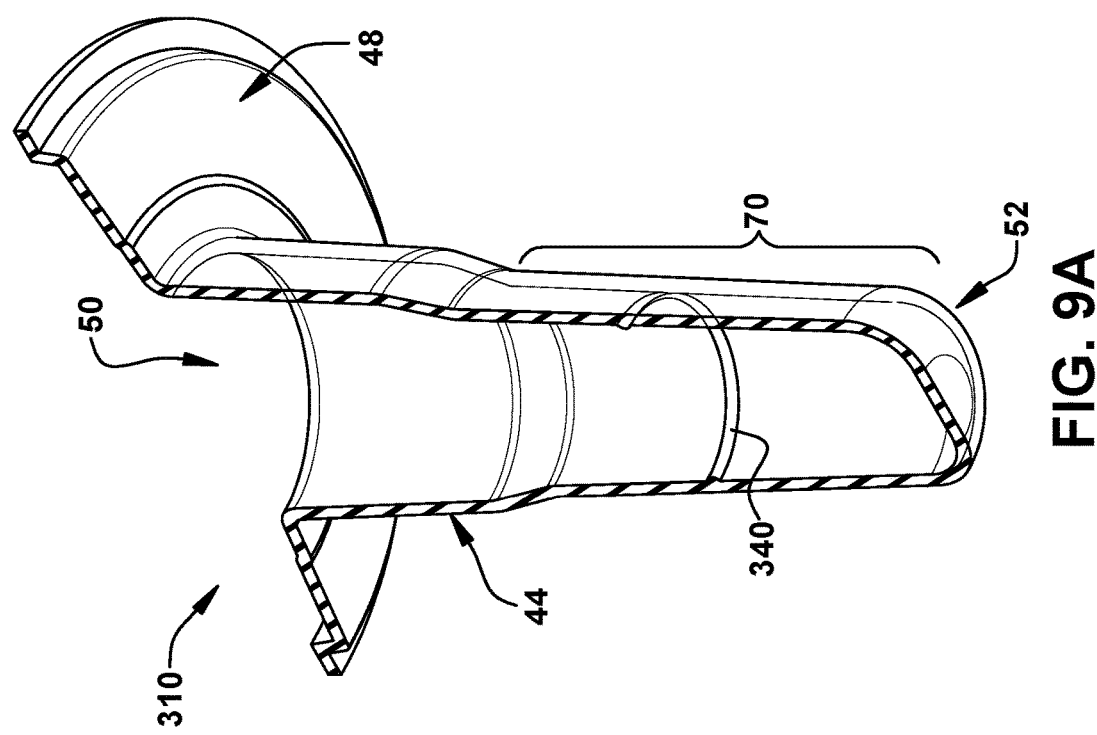

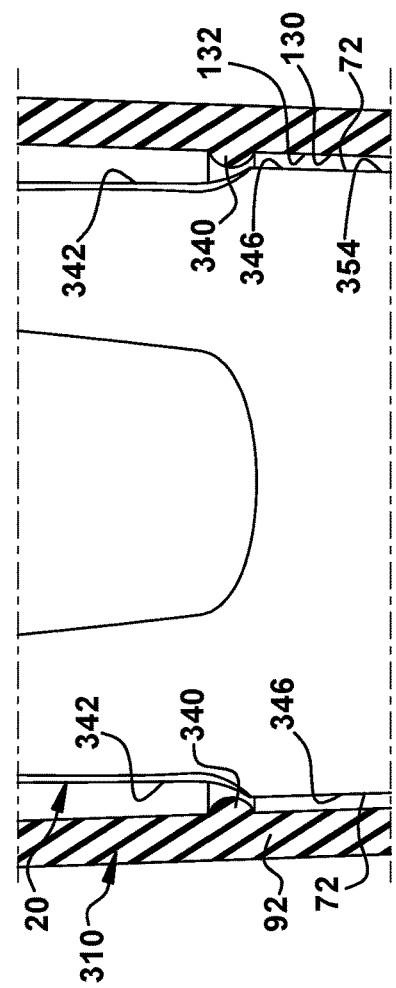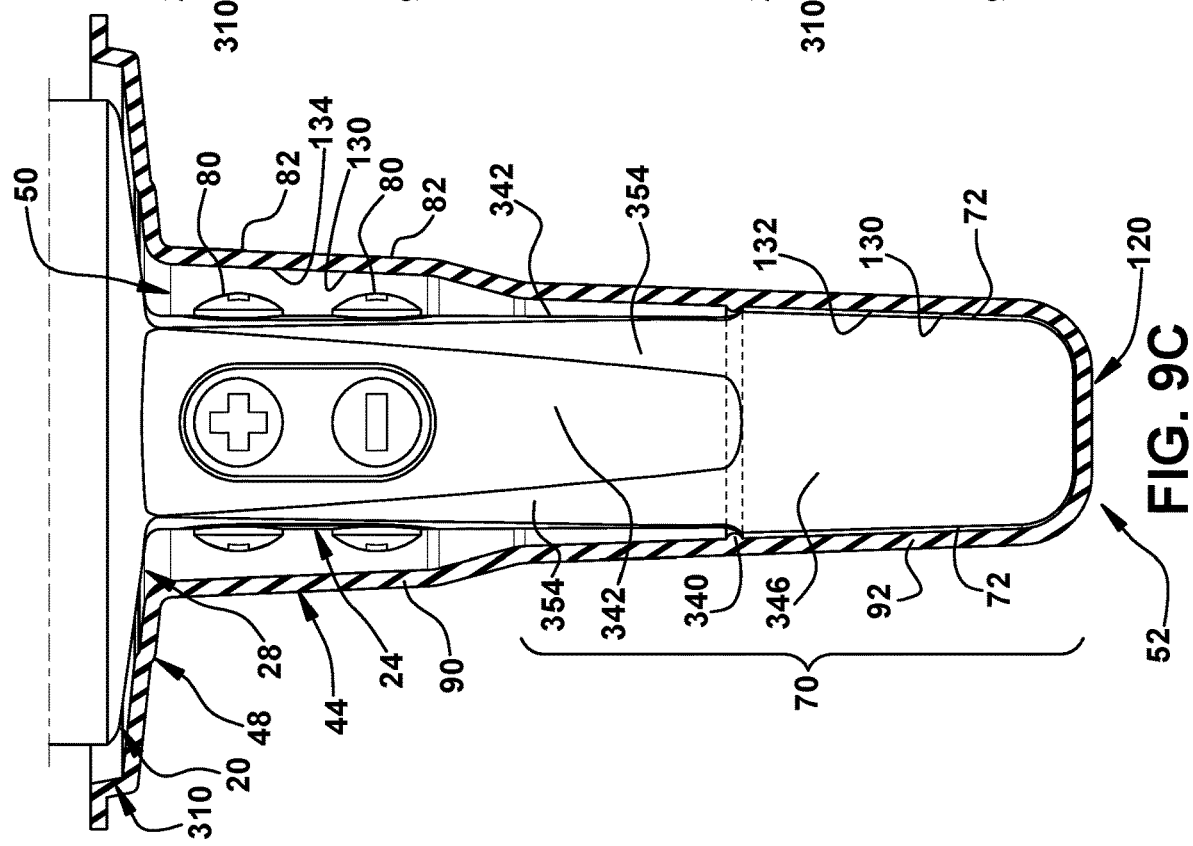

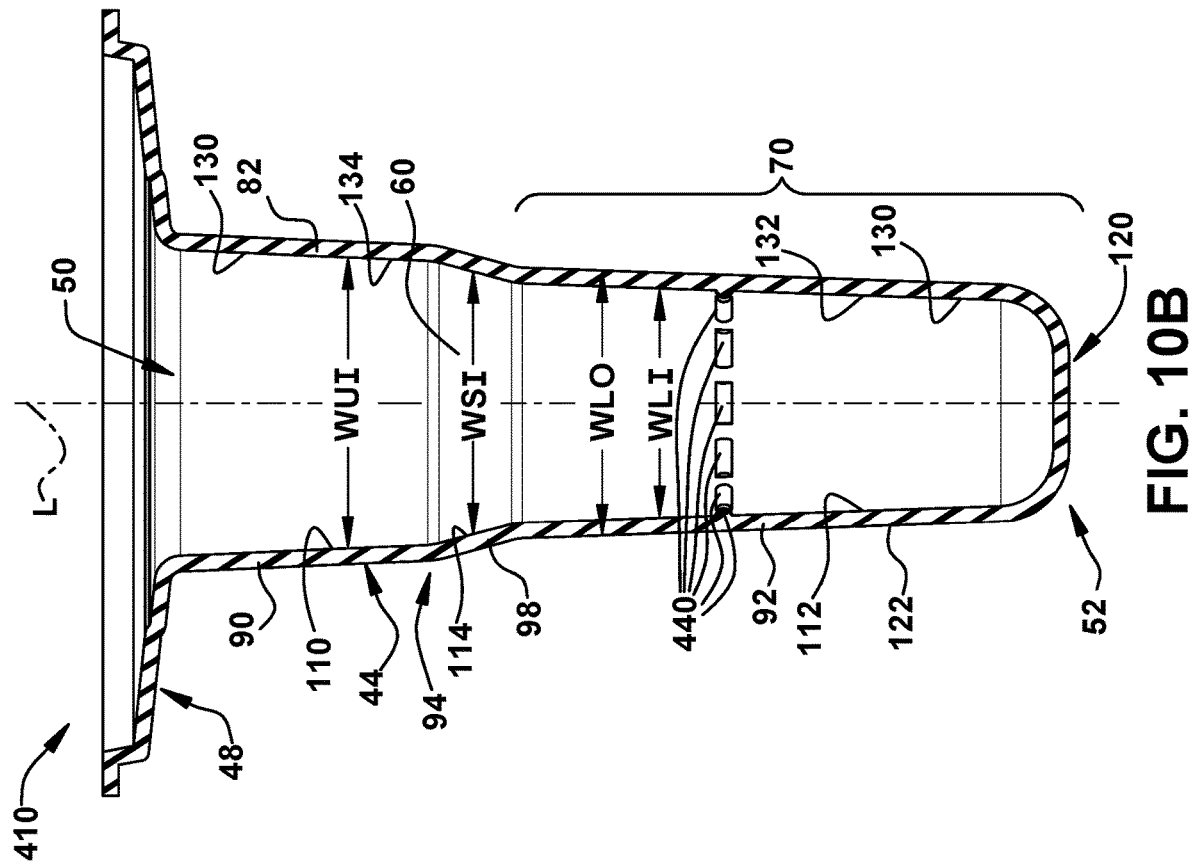
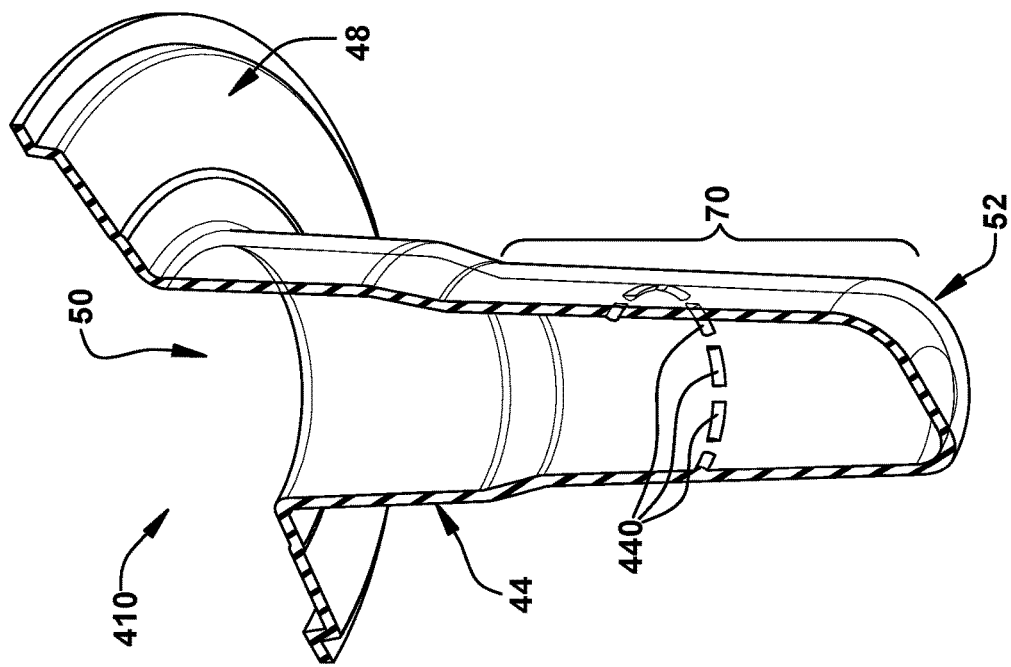
FIG. 10B
FIG. 10A

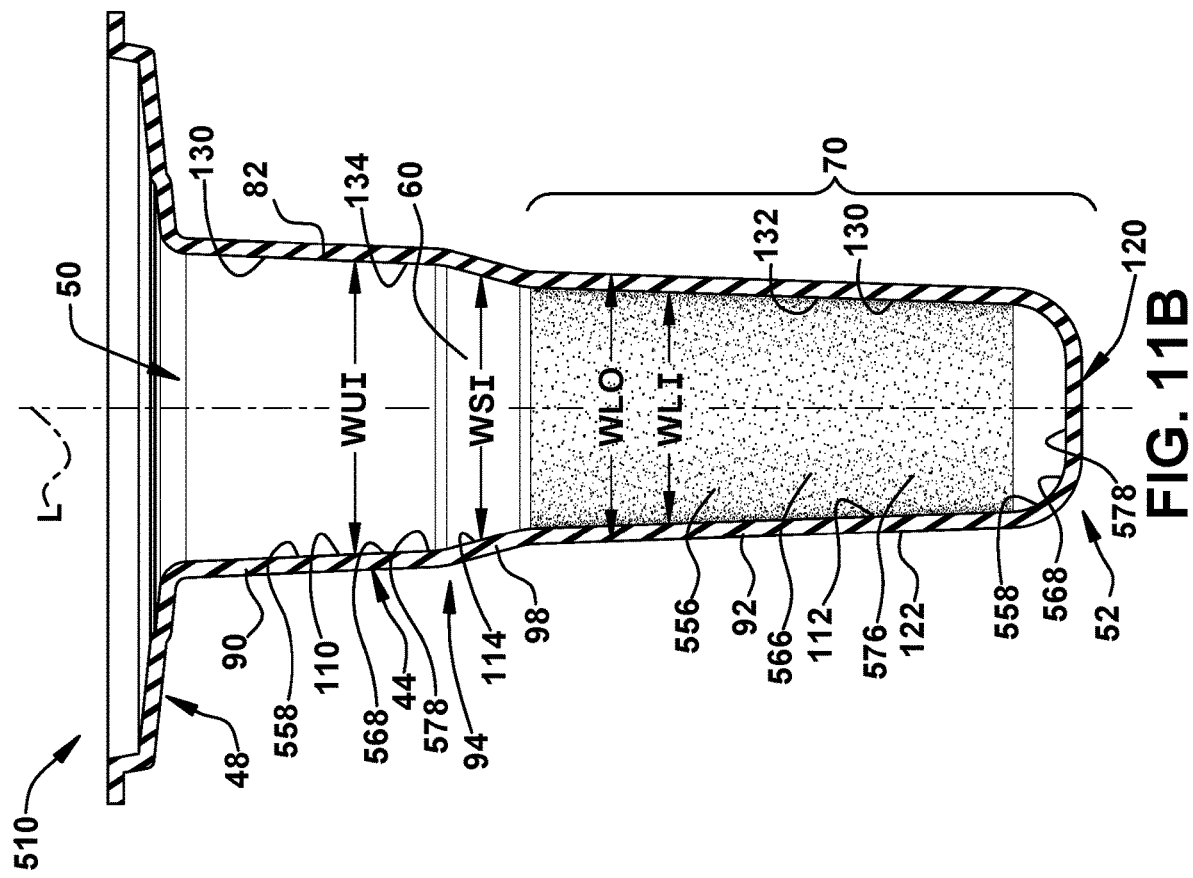
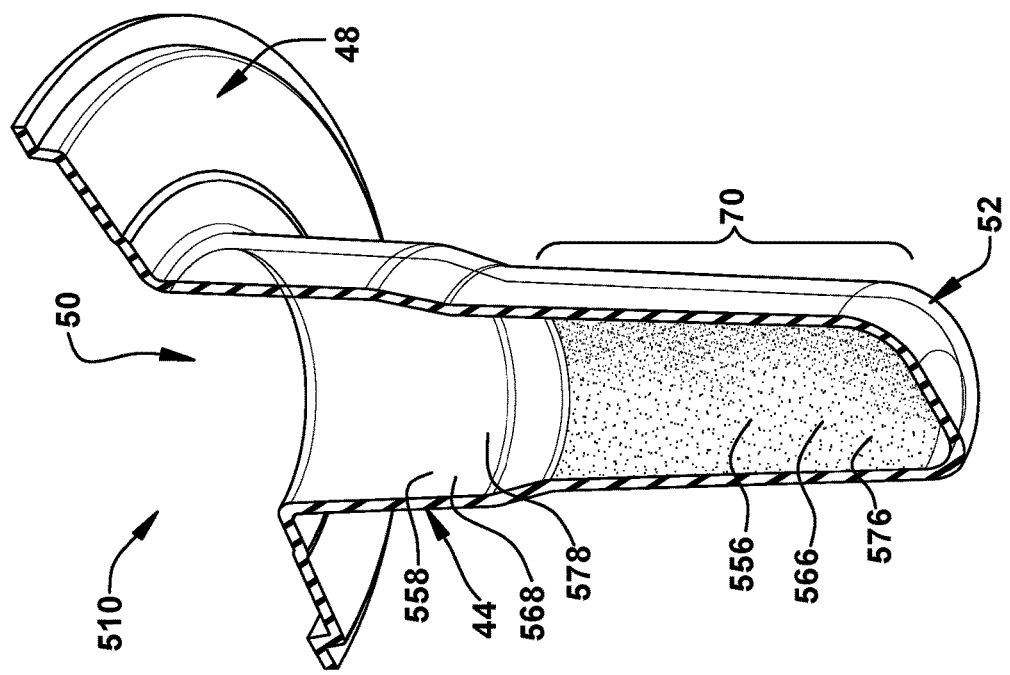

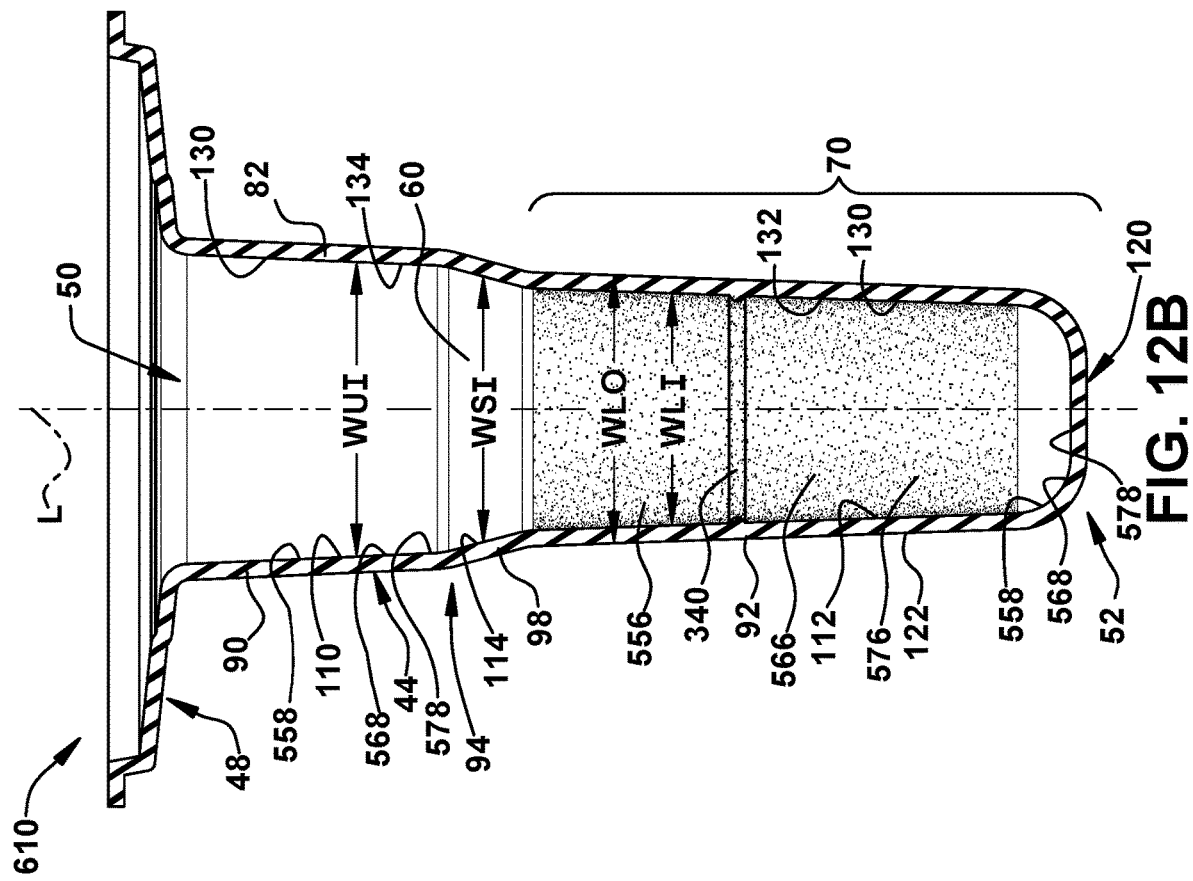
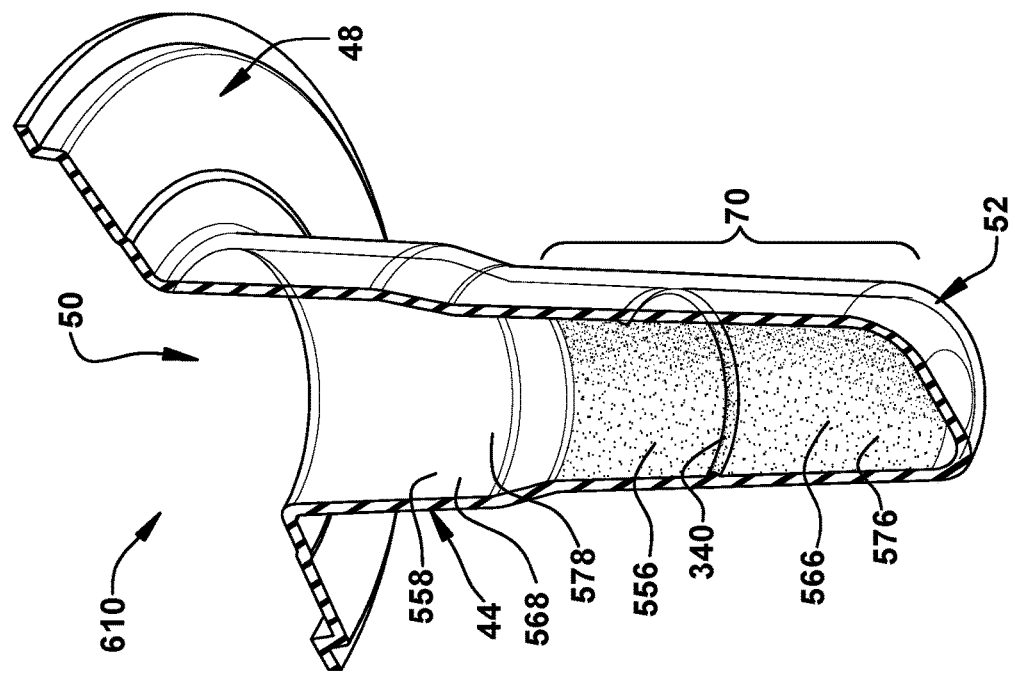

STERILIZABLE COVER FOR HANDLE OF ACCESSORY OF MEDICAL SUSPENDED CEILING ASSEMBLY

This application claims priority to U.S. Patent Application No. 63/338,070, filed May 4, 2022, which is hereby incorporated herein by reference in its entirety.

FIELD OF INVENTION

This application relates generally to a cover for a handle of an accessory of a medical suspended ceiling assembly, and more particularly to a sterilizable cover for the handle of the assembly.

BACKGROUND

Accessories of medical suspended ceiling assemblies typically include a handle to enable surgical personnel or other healthcare professionals to adjust the position of the accessory according to the needs of a specific medical procedure. To maintain a sterile operating environment, a sterilizable cover may be provided that fits over the handle, thus preventing the hands of surgical personnel from directly touching the handle. After the medical procedure, the sterilizable cover may then be sterilized for example in an autoclave, for later use.

Current sterilizable covers have various drawbacks in certain applications. Examples of current sterilizable covers include a hard-molded outer sleeve and a two-piece sterilizable cover assembly. The hard-molded sleeve type is installed over a handle core for rigid attachment. Hard-molded outer sleeves typically require a large form factor which can result in a handle covered by such a sleeve being larger and more difficult to grasp. Moreover, where surgeon control of a light head requires capacitive touch technology, responsiveness may not be reliable with surgical glove variability and fluids commonly incurred during a medical operation. Further, hard-molded sleeves require investment in injection mold tooling, oftentimes making them cost-prohibitive in the increasingly cost-sensitive health care industry.

The typical two-piece sterilizable cover may have a first piece in the form of a sterilizable metal component and a second piece in the form of a flexible insert. The sterilizable metal component includes a stem that is threaded onto a handle core and a base with openings that align with push control buttons in the handle core base. The flexible insert is sandwiched between the first piece and the handle core during assembly to cover the push control buttons and is designed to allow for interaction with the push control buttons by the flexibility in the insert. The chief shortcoming with the two-piece cover is that it requires disassembly for sterilization and then reassembly prior to being threaded back onto the handle core.

Accordingly, there remains a need for further contributions in this area of technology.

SUMMARY OF INVENTION

The application relates to a sterilizable cover that can be steam sterilized in a pressurized autoclave, dry heat sterilized, or chemically sterilized, after each use and reused over again. The sterilizable cover, by being made of flexible silicone rubber, is soft and flexible so that a control element of a handle underneath and covered by a corresponding portion of the sterilizable cover can be used simply by pressing the corresponding portion. A friction fit portion of the sterilizable cover creates a friction fit upon installation to retain the sterilizable cover on the handle. An annular flange portion aids in restoring the overall shape of the sterilizable cover over repeated use and sterilizations.

According to one aspect of the invention, a sterilizable cover is provided for a handle of an accessory of a medical suspended ceiling assembly, the handle having a generally tubular grip portion extending downward from a mounting structure of the accessory, the sterilizable cover including a generally tubular stem portion and an annular flange portion. The generally tubular stem portion has a sufficient size to be gripped by the human hand, and has a proximal end that is open and a distal end that is closed, and defines a cavity along a longitudinal axis for receipt therein of the handle grip portion. The generally tubular stem portion includes a friction fit portion that is configured to flex radially outwardly to create a friction fit with a portion of the handle grip portion upon receipt of the handle grip portion in the cavity of the generally tubular stem portion. The annular flange portion extends radially outwardly from the proximal end of the generally tubular stem portion. The stem portion and the annular flange portion are a single continuous piece of flexible silicone rubber.

Embodiments of the invention may include one or more of the following additional features separately or in combination.

The generally tubular stem portion may be tapered in a direction of the longitudinal axis from the proximal end to the distal end.

At least a portion of the silicone rubber may be translucent to enable the passage of light therethrough.

The silicone rubber may be configured to be steam sterilized in a pressurized autoclave, dry heat sterilized, or chemically sterilized, without degradation of the silicone rubber.

The silicone rubber may be configured to be resistant to temperatures between 70 and 570 degrees Fahrenheit.

At least the distal end of the generally tubular stem portion, or any other portion of the sterilizable handle, may have an optically clear area configured to enable camera imaging to pass therethrough.

The generally tubular stem portion may be circular in shape in axial cross section.

The generally tubular stem portion may have an upper generally tubular section protruding axially downward relative to the annular flange portion and a lower generally tubular section protruding axially downward relative to a bottom region of the upper generally tubular section.

An inner perimeter of the upper generally tubular section may be relatively wider in axial cross section than an inner perimeter of the lower generally tubular section.

The sterilizable may also include a shoulder that transitions radially inwardly from the inner perimeter of the upper generally tubular section to the inner perimeter of the lower generally tubular section.

An inner perimeter of the upper generally tubular section may be relatively wider in axial cross section than an outer perimeter of the lower generally tubular section.

The sterilizable cover may be stackable axially with respect to another sterilizable cover such that the lower generally tubular section of one sterilizable cover is nestable along at least a portion of the longitudinal axis within the cavity of the upper generally tubular section of another sterilizable cover.

The upper generally tubular section of the other sterilizable cover may be sized to receive the lower generally tubular section of the one sterilizable cover such that the bottom of the lower generally tubular section of the one sterilizable cover abuts a shoulder that transitions between the upper generally tubular section and the lower generally tubular section of the other sterilizable cover.

The length of the upper generally tubular section along the longitudinal axis may be in the range of about 1 inch to about 5 inches.

The length of the lower generally tubular section along the longitudinal axis may be in the range of about 1 inch to about 5 inches.

The outer diameter of the upper generally tubular section may be in the range of about 1 inch to about 4 inches.

The outer diameter of the lower generally tubular section may be in the range of about 0.5 inch to about 3 inches.

The lower generally tubular section may include one or more channels void of material on an inner surface of the lower generally tubular section in fluid communication with the cavity of the upper generally tubular section.

The friction fit portion may include at least a portion of an inner surface of the generally tubular stem portion.

The generally tubular stem portion may have an upper generally tubular section protruding axially downward relative to the annular flange portion and a lower generally tubular section protruding axially downward relative to a bottom region of the upper generally tubular section, and the friction fit portion may include at least a portion of an inner surface of the lower generally tubular section.

The sterilizable cover may further include at least one ridge projecting radially inward from an inner surface of the generally tubular stem portion.

The generally tubular stem portion may have an upper generally tubular section protruding axially downward relative to the annular flange portion and a lower generally tubular section protruding axially downward relative to a bottom region of the upper generally tubular section, and the sterilizable cover may further include at least one ridge projecting radially inward from an inner surface of the lower generally tubular section.

The at least one ridge when seen in a direction along the longitudinal axis may have a ring shape.

The at least one ridge may include a plurality of ridges that when seen in a direction along the longitudinal axis form a discontinuous ring shape that is partly discontinuous.

The at least one ridge may project radially inward from the inner surface to have a radially projecting width of about 0.01 inch to about 0.04 inch.

The at least one ridge may have a height along the longitudinal axis of about 0.02 inch to about 0.04 inch.

The at least one ridge may be located at a height along the longitudinal axis from the bottom of the generally tubular stem portion of about 1 inch to about 3 inches.

A first inner surface of the generally tubular stem portion may have a first textured surface, and a second inner surface of the generally tubular stem portion may have a second textured surface that is different from the first textured surface.

The first textured surface may have a first textured finish and the second textured surface may have a second textured finish, and the first textured finish may be relatively heavier than the second textured finish.

The second textured finish may be relatively smoother and less textured than the first textured finish.

The second textured finish may include an optically clear finish.

At least a portion of the first inner surface of the generally tubular stem portion may form part of the friction fit portion.

The generally tubular stem portion may have an upper generally tubular section protruding axially downward relative to the annular flange portion and a lower generally tubular section protruding axially downward relative to a bottom region of the upper generally tubular section, and the second inner surface may include an inner surface of the upper generally tubular section.

The first inner surface may include an inner surface of the lower generally tubular section.

The sterilizable cover may further include at least one ridge projecting radially inward from the first inner surface of the generally tubular stem portion.

The wall thickness of the generally tubular stem portion may be in the range of about 0.04 inch to about 0.16 inch.

The silicone rubber of the sterilizable cover may have a Shore A hardness of about 20 to about 70.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

FIG. 1A is a perspective view of a sterilizable cover in accordance with an embodiment of the invention.

FIG. 1B is a cross-sectional perspective view of the FIG. 1A sterilizable cover.

FIG. 2A is a side elevational view of the FIG. 1A sterilizable cover.

FIG. 2B is a side cross-sectional view of the FIG. 1A sterilizable cover as viewed from the plane 2B-2B in FIG. 2A.

FIG. 5 is a perspective view of the FIG. 1A sterilizable cover shown installed on a handle of an accessory of a medical suspended ceiling assembly, showing light of covered illuminated control elements of the accessory handle passing through the sterilizable cover.

FIG. 6 is a view showing a plurality of the FIG. 1A sterilizable covers stacked and nested.

FIG. 7A is a side cross-sectional view of the FIG. 1A sterilizable cover as viewed from the plane 2B-2B in FIG. 2A, showing a friction fit of the sterilizable cover relative to a handle underneath.

FIG. 7B is a side cross-sectional view of the FIG. 1A sterilizable cover as viewed from the plane 2B-2B in FIG. 2A, showing a release feature of the sterilizable cover relative to a handle underneath.

FIG. 8A is a perspective view of a sterilizable cover in accordance with another embodiment of the invention.

FIG. 8B is a cross-sectional perspective view of the FIG. 8A sterilizable cover.

FIG. 9A is a cross-sectional perspective view of a sterilizable cover in accordance with another embodiment of the invention.

FIG. 9B is a side cross-sectional view of the FIG. 9A sterilizable cover.

FIG. 9C is a side cross-sectional view of the FIG. 9A sterilizable cover, showing a friction fit of the sterilizable cover relative to a handle underneath.

FIG. 9D is an enlarged view of a ridge of the FIG. 9A sterilizable cover.

FIG. 9E is an enlarged view of the ridge of the FIG. 9A sterilizable cover, with the sterilizable cover positioned higher relative to the handle than in the position shown in FIG. 9D.

FIG. 10A is a cross-sectional perspective view of a sterilizable cover in accordance with another embodiment of the invention.

FIG. 10B is a side cross-sectional view of the FIG. 10A sterilizable cover.

FIG. 11A is a cross-sectional perspective view of a sterilizable cover in accordance with another embodiment of the invention.

FIG. 11B is a side cross-sectional view of the FIG. 11A sterilizable cover.

FIG. 12A is a cross-sectional perspective view of a sterilizable cover in accordance with another embodiment of the invention.

FIG. 12B is a side cross-sectional view of the FIG. 12A sterilizable cover.

DETAILED DESCRIPTION

Figure 2D:
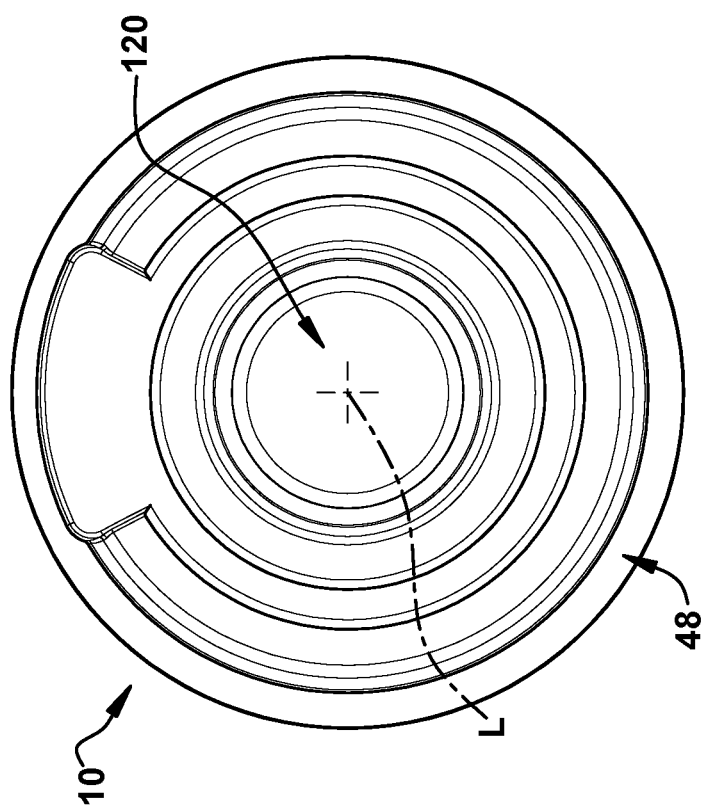
FIG. 2D is a bottom view of the FIG. 1A sterilizable cover as viewed from the plane 2D-2D in FIG. 2A.
Figure 2C:
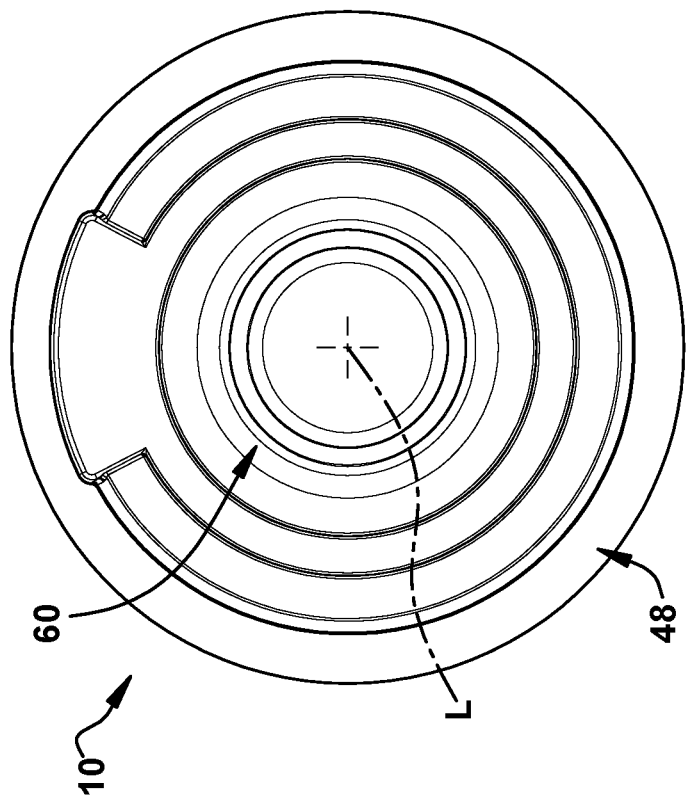
FIG. 2C is a top plan view of the FIG. 1A sterilizable cover as viewed from the plane 2C-2C in FIG. 2A.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

FIGS. 1A-7B show a sterilizable cover 10 for a handle 20 of an accessory 22 of a medical suspended ceiling assembly in accordance with an embodiment of the invention. Herein, the sterilizable cover 10 is described in connection with a handle of a surgical light head of a suspended surgical lighting system. It is contemplated that the sterilizable cover 10 may be applicable to a handle of any type of accessory 22 of a medical suspended ceiling assembly, particularly for which an integrated handle user interface is provided for controlling the handle, the accessory, or other components of the ceiling assembly. In some embodiments, the sterilizable cover 10 may be suitable to cover a handle of a dedicated suspension arm of a medical suspended ceiling assembly.

The handle 20, which is shown with the sterilizable cover 10 installed thereon in FIGS. 5 and 7A-7B, has a generally tubular grip portion 24 extending downward from a mounting structure 26 of the accessory 22, and an annular flange portion 28 extending radially outwardly from the grip portion 24 in proximity to the mounting structure 26. The sterilizable cover 10 includes a generally tubular stem portion 44 and an annular flange portion 48, which respectively cover the grip portion 24 and flange portion 28 of the handle 20. In some embodiments, the accessory handle 20 may not include a flange portion 28, in which case the flange portion 48 of the sterilizable cover 10 may cover a portion of the mounting structure 26 of the accessory 22. The generally tubular stem portion 44 of the sterilizable cover 10, and the handle 20 on which it is installed, has a sufficient size to be gripped by the human hand meaning that the outermost diameter or perimeter of the generally tubular stem portion 44 is selected to enable a human hand to be comfortably wrapped around the generally tubular stem portion 44. As shown in FIGS. 1A-1B, 2A-2D and 7A-7B, the generally tubular stem portion 44 has a proximal end 50 that is open and a distal end 52 that is closed. The generally tubular stem portion 44 defines a cavity 60 along a longitudinal axis L-L for receipt therein of the handle grip portion 24. The generally tubular stem portion 44 also includes a friction fit portion 70 that is configured to flex radially outwardly to create a friction fit with a corresponding portion 72 of the handle grip portion 24 upon receipt of the handle grip portion 24 in the cavity 60 of the generally tubular stem portion 44. The annular flange portion 48 extends radially outwardly from the proximal end 50 of the generally tubular stem portion 44. The generally tubular stem portion 44 and the annular flange portion 48 are a single continuous piece of flexible silicone rubber.

As will be described in greater detail below, several advantages may be realized by the sterilizable cover 10 in accordance with the invention. For example, because the sterilizable cover 10 is constructed of silicone rubber, the sterilizable cover 10 can be steam sterilized in a pressurized autoclave, dry heat sterilized, or chemically sterilized, after each use and reused over again. Moreover, the sterilizable cover 10, by being made of flexible silicone rubber, is soft and flexible so that a control element 80 of the handle 20 underneath and covered by a corresponding portion 82 of the sterilizable cover 10 can be used simply by pressing the corresponding portion 82. The friction fit portion 70 creates a friction fit upon installation to retain the sterilizable cover 10 on the handle 20. The annular flange portion 48 at the proximal end 50 of the generally tubular stem portion 44 aids in restoring the shape of the generally tubular stem portion 44 and thus the overall shape of the sterilizable cover 10 over repeated use and sterilizations.

Turning initially then to FIGS. 1A-1B, 5 and 7A-7B, the sterilizable cover 10 is configured to be installed over an accessory handle 20 that includes, for example, integrated control elements 80. The control elements 80 may be configured to provide an intuitive and effective user interface for the handle 20 for controlling any aspect of the system, such as attributes of the accessory for example attributes of the light emitted from the accessory-surgical light head 22, or attributes of a camera mounted within the handle 20, or attributes of other components of the medical suspended ceiling assembly. The control elements 80 may be in the form of push control buttons that include one or more of tactile, auditory, haptic, and visible feedback capabilities or modes. Visible feedback may be in the form of illuminated control buttons that become more bright or less bright in response to user commands. FIG. 5 shows an example of illuminated control buttons 80.

The generally tubular stem portion 44 and the annular flange portion 48 of the sterilizable cover 10 form a single continuous piece of silicone rubber that is soft to the touch. For example, the silicone rubber may have a Shore A hardness of about 20 to about 70. The single piece construction avoids the need for disassembly and reassembly of the sterilizable cover 10 for each medical procedure and sterilization process, as is the case with the afore mentioned two-piece sterilizable cover assemblies.

The silicone rubber may be any desired color and may be configured to be non-reactive, stable, and resistant to temperatures between 70 and 570 degrees Fahrenheit. The material properties of silicone rubber enable the sterilizable cover to be steam sterilized in a pressurized autoclave, dry heat sterilized, or chemically sterilized, without degradation of the silicone rubber and the sterilizable cover 10 even through thousands of sterilization cycles. As such, the sterilizable cover 10 can be reused reliably.

Figure 4:
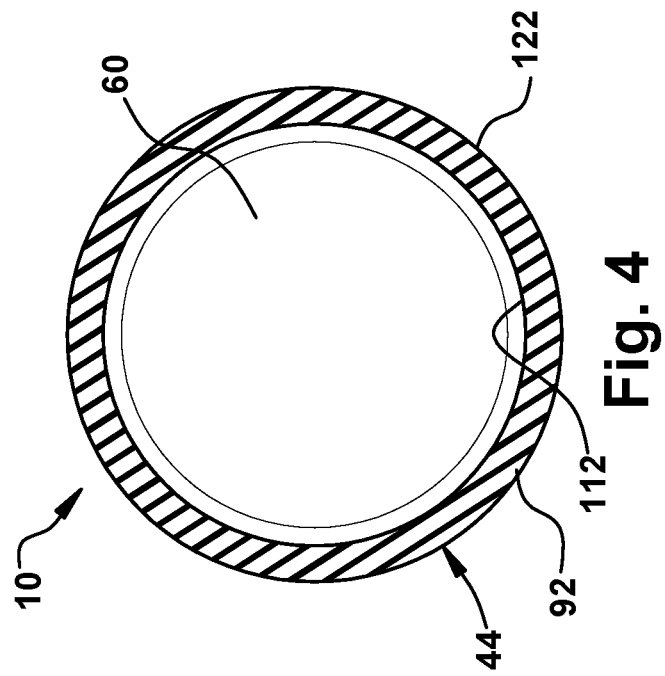
FIG. 4 is an axial cross-sectional view of the FIG. 1A sterilizable cover as viewed from the plane 4-4 in FIG. 2A.
Figure 3:
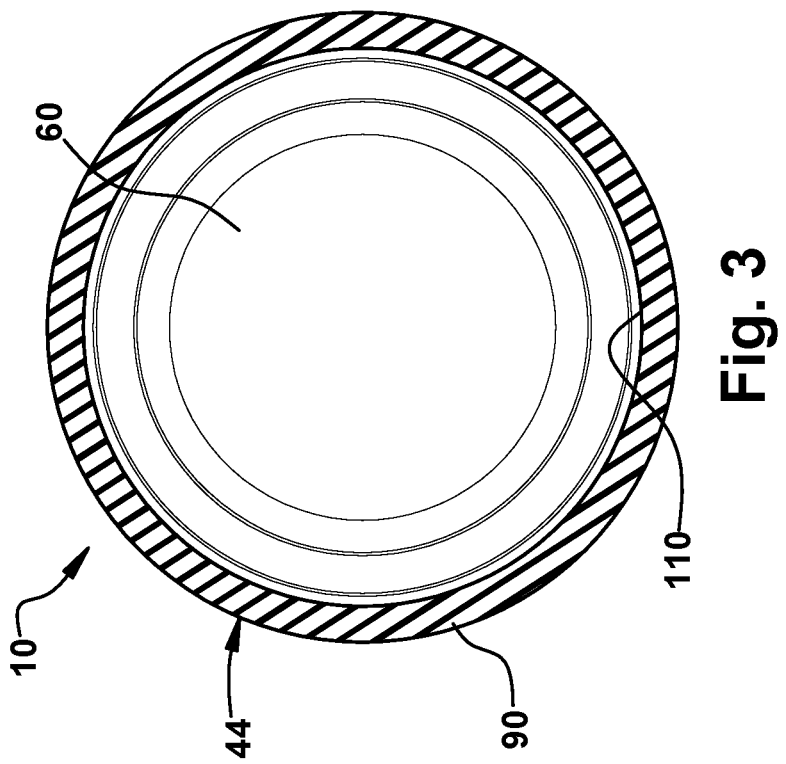
FIG. 3 is an axial cross-sectional view of the FIG. 1A sterilizable cover as viewed from the plane 3-3 in FIG. 2A.

Referring next to FIGS. 2A-2D, 3 and 4, the generally tubular stem portion 44 is tapered in a direction of the longitudinal axis L-L from the proximal end 50 to the distal end 52 of the generally tubular stem portion 44. As shown in FIGS. 3 and 4, the illustrated stem portion 44 is circular in shape in axial cross section, that is when seen in a direction along the longitudinal axis L-L, although it will be appreciated that the generally tubular stem portion 44 may have any generally tubular shape in axial cross section including generally square tubular in shape with curved corners, generally triangular tubular in shape with curved corners, and/or an elliptical tubular shape. The generally tubular stem portion 44 has an upper generally tubular section 90 protruding axially downward relative to the annular flange portion 48 and a lower generally tubular section 92 protruding axially downward relative to a bottom region 94 of the upper generally tubular section 90. An inner perimeter 110 of the upper generally tubular section 90 is relatively wider in axial cross section than an inner perimeter 112 of the lower generally tubular section 92. In some embodiments, the upper generally tubular section 90 may have an outer diameter in the range of about 1 inch to about 4 inches, a length along the longitudinal axis L-L in the range of about 1 inch to about 5 inches, and a wall thickness in the range of about 0.04 inch to about 0.16 inch. The lower generally tubular section 92 may have an outer diameter in the range of about 0.5 inch to about 3 inches, a length along the longitudinal axis L-L in the range of about 1 inch to about 5 inches, and a wall thickness in the range of about 0.04 inch to about 0.16 inch.

In the illustrated embodiment, the sterilizable cover 10 is provided with a shoulder 98 that transitions axially downwardly and radially inwardly from the inner perimeter 110 of the upper generally tubular section 90 to the inner perimeter 112 of the lower generally tubular section 92. Thus, in the illustrated generally tubular stem portion 44, a width WUI, or diameter, of the inner perimeter 110 of the upper generally tubular section 90 narrows from the annular flange portion 48 to the shoulder 98; a width WSI, or diameter, of an inner perimeter 114 of the shoulder 98 narrows from the upper generally tubular section 90 to the lower generally tubular section 92; and a width WLI, or diameter, of the inner perimeter 112 of the lower generally tubular section 92 narrows from the shoulder 98 to the distal end 52 of the generally tubular stem portion 44. In some embodiments, the shoulder 98 may be omitted and the sterilizable cover 10 may comprise a smooth or linear transition from the inner perimeter 110 of the upper generally tubular section 90 to the inner perimeter 112 of the lower generally tubular section 92.

The sterilizable cover 10 is configured to enable user access to existing integrated handle user interfaces of the handle 20 underneath the sterilizable cover 10, aided in part by the silicone rubber construction of the sterilizable cover 10. In FIG. 5, for example, the upper generally tubular section 90 incorporates the portion 82 corresponding to the control elements 80 of the handle 20 underneath. The upper generally tubular section 90, owing to its silicone rubber construction and generally tubular geometry, is configured to flex radially inwardly in response to a user pressing the portion 82 and the underlying control element 80 and to return to an unflexed state in response to releasing of the control element 80 and corresponding portion 82, as shown respectively in FIGS. 7A and 7B. In this way, the sterilizable cover 10 can maintain the utility of the control elements 80 of the handle 20, for example, the afore mentioned push buttons equipped with tactile, auditory, haptic, and/or visible feedback capabilities.

As noted previously, the annular flange portion 48 may aid in restoring the shape of the sterilizable cover 10, which restoration may include restoring the upper generally tubular section 90 and the portion 82 thereof to an unflexed state. For depressible type control elements, restoring the shape of the sterilizable cover 10 may also facilitate the return of the depressible control element to its original position after release.

The sterilizable cover 10 may be configured in whole or in part with silicone rubber that is translucent. For example, in FIG. 5 the upper generally tubular section 90 may be translucent. In some embodiments, the translucent portion is configured to allow a user to see the sterile control elements 80 covered by the sterilizable cover 10. In some embodiments, the translucent portion is configured to allow the passage of light from covered illuminated components such as the illuminated control elements 80 shown in FIG. 5. In still other embodiments, and as will be described in greater detail with respect to FIGS. 8A-8B, the generally tubular stem portion 44 may have an optically clear area 120, or the entire stem portion 44 itself or entire sterilizable cover 10 itself may be optically clear, to enable camera imaging to pass therethrough.

The sterilizable cover 10 may also be configured to be nestable and/or stackable. As shown in FIG. 2B, for example, the width WUI of the inner perimeter 110 of the upper generally tubular section 90 is relatively wider in axial cross section than a width WLO, or diameter, of an outer perimeter 122 of the lower generally tubular section 92. In some embodiments, at least a portion of the lower generally tubular section 92 of one sterilizable cover 10 is configured to be inserted into the cavity 60 of the upper generally tubular section 90 of another sterilizable cover 10, which may facilitate nesting and stacking of multiple sterilizable covers 10. Referring to FIG. 6, for example, a first sterilizable cover 10A may be stacked axially with respect to a second sterilizable cover 10B such that the lower generally tubular section 92 of the second sterilizable cover 10B is nested along a portion of the longitudinal axis L-L within the cavity 60 of the upper generally tubular section 90 of the first sterilizable cover 10A.

In some embodiments, the cavity 60 of the upper generally tubular section 90 of the first sterilizable cover 10A may be sized to receive the lower generally tubular section 92 of the second sterilizable cover 10B such that the bottom of the lower generally tubular section 92 of the second sterilizable cover 10B abuts the shoulder 98 that transitions between the upper generally tubular section 90 and the lower generally tubular section 92 of the first sterilizable cover 10A. FIG. 6 shows five sterilizable covers 10A, 10B, 10C, 10D, 10E stacked and nested together in this manner. Referring to the bottom of FIG. 6, the abutting contact with the shoulder 98 also provides a gap G between adjacent stacked annular flange portions 48 of the respective sterilizable covers 10A, 10B, 10C, 10D, 10E, enabling a user to easily position the hand between the annular flange portions 48 to separate adjacent stacked sterilizable covers 10A, 10B, 10C, 10D, 10E.

FIGS. 7A-7B show a release feature of the sterilizable cover 10 in accordance with an embodiment of the invention. As earlier described, and as shown for example in FIG. 7A, the generally tubular stem portion 44 of the sterilizable cover 10 includes a friction fit portion 70 that frictionally engages a corresponding portion 72 of the handle grip portion 24 to retain the sterilizable cover 10 on the handle 20. In the illustrated embodiment, the friction fit portion 70 includes at least a portion of an inner surface 130 of the generally tubular stem portion 44, and more particularly at least a portion of an inner surface 132 of the lower generally tubular section 92 of the generally tubular stem portion 44. The release feature is configured in the following way, it being understood that other ways are also contemplated.

The release feature may be incorporated into the generally tubular stem portion 44 by the relationship between the upper generally tubular section 90, the lower generally tubular section 92, and the shoulder 98 therebetween. As shown in FIG. 7B, the generally tubular stem portion 44 is configured such that a squeeze force SF, and in some cases also a twist force TF about the longitudinal axis L-L, applied to the upper generally tubular section 90 causes the upper part of the shoulder 98 to flex radially inwardly and, via force transfer through the shoulder 98, imparts a radially outward force R to the lower generally tubular section 92 including at the friction fit portion 70 of the generally tubular stem portion 44. As a result, a gap H is formed between portions of the lower generally tubular section 92 and the handle grip portion 24, thereby to loosen the friction fit therebetween, thus releasing the sterilizable cover 10 from frictional engagement with the handle 20, or at least reducing the frictional engagement between the inner surface 130 of the generally tubular step portion 44 and the handle grip portion 24, and enabling easy removal of the sterilizable cover 10 from the handle 20 by simply pulling the sterilizable cover axially downward. Once removed, the annular flange portion 48 at the proximal end 50 of the generally tubular stem portion 44 may aid in restoring the generally tubular shape of the generally tubular stem portion 44, including the friction fit portion 70 flexing radially inwardly to its unflexed state, thereby restoring the overall shape of the sterilizable cover 10. As will be appreciated, the upper generally tubular section 90 is configured to flex inward without "grabbing" or frictionally engaging the handle 20 whereas grabbing the lower generally tubular section 92 reinforces the grip.

FIGS. 8A-8B show a sterilizable cover 210 in accordance with another embodiment of the invention. The FIG. 8A sterilizable cover 210 is in many respects similar to the above-described FIG. 1A sterilizable cover 10, and consequently the same reference numerals are used to denote structures corresponding to similar structures in the sterilizable cover 10. In addition, the foregoing description of the FIG. 1A sterilizable cover 10 is equally applicable to the FIG. 8A sterilizable cover 210 except as noted below. Moreover, it will be appreciated upon reading and understanding the specification that aspects of the sterilizable covers 10, 210 may be substituted for one another or used in conjunction with one another where applicable.

Turning then to FIGS. 8A-8B, the sterilizable cover 210 is made of silicone rubber and is configured to cover an accessory handle that incorporates a camera therein, also referred to as a camera handle. The generally tubular stem portion 44 of the sterilizable cover 210 has an optically clear area 120 at its distal end 52 that is configured to enable camera imaging to pass therethrough. The optically clear area 120 may be circular in shape in axial cross section, as shown, or any shape suited for a camera supported within the handle covered by the sterilizable cover 210. In the illustrated embodiment, the sterilizable cover 210 is a homogeneous design wherein the optically clear area 120, the upper and lower generally tubular sections 90, 92, and the annular flange portion 48, are made of the same silicone rubber material, that is as a monolithic one-piece unit, while the optically clear area 120 is configured to be optically clear. In some embodiments, the entire stem portion 44, or the entire sterilizable cover 210, may be made to be optically clear to enable camera imaging to pass therethrough. In some embodiments, surface finishing may be used to form the optically clear area 120, or areas.

The sterilizable cover 210 may also be equipped with channels 214 void of material on the inner surface 130 of the lower generally tubular section 92 to be in fluid communication with the cavity 60 of the upper generally tubular section 90. In the FIG. 8A embodiment, the channels 214 extend axially substantially in the direction of the longitudinal axis L-L although it will be appreciated that the channels 214 may extend along any path, linear or nonlinear, from the lower generally tubular section 92 to being in fluid communication with the cavity 60 of the upper generally tubular section 90. The illustrated embodiment has four channels 214 equally angularly spaced apart around the circumference of the lower generally tubular section 92. The illustrated channels 214 are 0.063 inch in width although other widths are contemplated, for example, in the range of 0.016 to 0.25 inch. In some embodiments, the channels 214 may be configured as vents. In this way, upon squeezing the upper generally tubular section 90 air may be directed from the upper generally tubular section 90 to the lower generally tubular section 92 via the channels 214 to release or reduce the frictional engagement between the sterilizable cover 210 and the handle, thereby aiding in removal of the sterilizable cover 210 from the handle. Channels 214 may be provided on the inner surface 134 of the upper generally tubular section 90 and/or the inner surface 132 of the lower generally tubular section 92 and/or an inner surface of the shoulder 98 for such venting purposes to aid in removal of the sterilizable cover 210 from the handle 20. The aforedescribed sterilizable cover 10 may also be provided with such channels 214.

In some embodiments, ribs may be provided on the outer or inner surface of the upper generally tubular section 90 and/or the lower generally tubular section 92 and/or the shoulder 98 to add stiffness to the sterilizable covers 10, 210, particularly in the direction of the longitudinal axis L-L, to aid in preventing the sterilizable covers 10, 210 from buckling axially during installation and removal.

FIGS. 9A-9E show a sterilizable cover 310 in accordance with another embodiment of the invention. The FIG. 9A sterilizable cover 310 is in many respects similar to the above-described FIG. 1A and FIG. 8A sterilizable covers 10, 210 and consequently the same reference numerals are used to denote structures corresponding to similar structures in the sterilizable cover 310. In addition, the foregoing description of the FIG. 1A and FIG. 8A sterilizable covers 10, 210 is equally applicable to the FIG. 9A sterilizable cover 310 except as noted below. Moreover, it will be appreciated upon reading and understanding the specification that aspects of the sterilizable covers 10, 210, 310 may be substituted for one another or used in conjunction with one another where applicable.

Turning then to FIGS. 9A-9E, the sterilizable cover 310 includes at least one ridge 340 projecting radially inward from the inner surface 130 of the generally tubular stem portion 44. In the illustrated embodiment, the ridge 340 projects radially inward from the inner surface 132 of the lower generally tubular section 92. As will be appreciated, the ridge 340 alternately may be provided to project from the inner surface 134 of the upper generally tubular section 90. Referring to FIG. 9A, which shows only half of the ridge 340 owing to the view being cross-sectional, the illustrated ridge 340 is ring shape in axial cross section, that is when seen in a direction along the longitudinal axis L-L. Ring shape as used herein means an annular shape, a hollow circle shape, a bracelet shape, and/or a donut shape. It will be appreciated that the ridge 340 may have any ring shape in axial cross section including square ring shape with curved corners, triangular ring shape with curved corners, and/or an elliptical ring shape.

In some embodiments, the ridge 340 may project radially inward from the inner surface 130 of the generally tubular stem portion 44 to have a radially projecting width of about 0.01 inch to about 0.04 inch. Also, in some embodiments, the ridge 340 may have a height along the longitudinal axis L-L of about 0.02 inch to about 0.04 inch. The ridge 340 may be located at a height along the longitudinal axis L-L from the bottom of the generally tubular stem portion 44 of about 1 inch to about 3 inches. This enables a user to grip the lower portion of the generally tubular stem portion 44 between the thumb and index finger below the location of the ridge 340.

As shown in FIGS. 5 and 9C-9E, the generally tubular grip portion 24 may include recesses 342 that are recessed relative to an outer surface 346 of the generally tubular grip portion 24. The illustrated embodiment has four such recesses 342 and four intermediate outer surface portions 354 equally angularly spaced apart around the outer surface 346 of the handle 20. As shown in FIGS. 9D and 9E, the ridge 340 may be configured on the inner surface 130 of the generally tubular stem portion 44 of the sterilizable cover 310 such that as a user installs the sterilizable cover 310 onto the handle 20, that is along the longitudinal axis L-L, the ridge 340 initially flexes radially outwardly as shown in FIG. 9D, and then as the ridge 340 is further urged upward onto the handle 20 and beyond the lower edges of the angularly spaced four recesses 342 the ridge 340 at the locations of the angularly spaced four recesses 342 unflexes at least partially, that is flexes back radially inwardly as shown in FIG. 9E. The inventors found that this radially outward and radially inward flexure of the ridge 340 provides feedback to the user that the sterilizable cover 310 is installed on the handle 20 and thus is ready for use.

Like the afore described friction fit portion 70, the ridge 340 may be configured to flex radially outwardly to create a friction fit with a portion of the generally tubular grip portion 24 of the handle 20 upon receipt of the generally tubular grip portion 24 in the cavity 60 of the generally tubular stem portion 44. Thus, for example, in the illustrated embodiment when the ridge 340 unflexes the ridge 340 engages the four intermediate outer surface portions 354 to create a friction fit with the corresponding portion 72 of the handle grip portion 24 upon receipt of the handle grip portion 24 in the cavity 60 of the generally tubular stem portion 44.

In some embodiments, the ridge 340 may provide feedback to a user without creation of a friction fit with a corresponding portion of the generally tubular grip portion 24 of the handle 20. For example, in an alternate embodiment, the handle may have a circumferential recess similar in radial depth to the four recesses 342 such that as the ridge 340 is urged beyond the lower edge of the recess the ridge 340 unflexes, that is flexes back radially inwardly to reside within the recess without frictionally engaging the generally tubular grip portion 24 of the handle 20. The radially outward and radially inward flexure of the ridge 340 provides feedback to the user that the sterilizable cover 310 is installed on the handle 20 and thus is ready for use. In some embodiments, the ridge may provide feedback to a user without recesses 342 or a recess. For example, the generally tubular grip portion 24 of the handle 20 may not include recesses 342 and the ridge 340 still provides feedback to user by the user pushing up against the sterilizable cover 310 against the ridge 340 on the inner surface 130 of the generally tubular stem portion 44.

As was noted above, the at least one ridge 340 may be provided at any portion of the generally tubular stem portion 44 whether the lower generally tubular section 92 thereof as shown or the upper generally tubular section 90.

FIGS. 10A-10B show a sterilizable cover 410 in accordance with another embodiment of the invention. The FIG. 10A sterilizable cover 410 is in many respects similar to the above-described FIG. 1A, FIG. 8A, FIG. 9A sterilizable covers 10, 210, 310 and consequently the same reference numerals are used to denote structures corresponding to similar structures in the sterilizable cover 410. In addition, the foregoing description of the FIG. 1A, FIG. 8A, FIG. 9A sterilizable covers 10, 210, 310 is equally applicable to the FIG. 10A sterilizable cover 410 except as noted below. Moreover, it will be appreciated upon reading and understanding the specification that aspects of the sterilizable covers 10, 210, 310, 410 may be substituted for one another or used in conjunction with one another where applicable.

Turning then to FIGS. 10A-10B, the sterilizable cover 410 includes a plurality of ridges 440 projecting radially inward from the inner surface 130 of the generally tubular stem portion 44. In the illustrated embodiment, the plurality of ridges 440 project radially inward from the inner surface 132 of the lower generally tubular section 92. As will be appreciated, the plurality of ridges 440 alternately may be provided to project from the inner surface 134 of the upper generally tubular section 90. Referring to FIG. 10A, which shows only half of the plurality of ridges 440 owing to the view being cross-sectional, the illustrated plurality of ridges 440 form in axial cross section, that is when seen in a direction along the longitudinal axis L-L, a discontinuous ring shape that is partly discontinuous. Discontinuous ring shape as used herein means a discontinuous annular shape, a discontinuous hollow circle shape, a discontinuous bracelet shape, and/or a discontinuous donut shape. It will be appreciated that the plurality of ridges 440 may have any discontinuous ring shape in axial cross section including discontinuous square ring shape with curved corners, discontinuous triangular ring shape with curved corners, and/or discontinuous elliptical ring shape.

In some embodiments, the plurality of ridges 440 may project radially inward from the inner surface 130 of the generally tubular stem portion 44 to have a radially projecting width of about 0.01 inch to about 0.04 inch. Also, in some embodiments, the plurality of ridges 440 may have a height along the longitudinal axis L-L of about 0.02 inch to about 0.04 inch. The plurality of ridges 440 may be located at a height along the longitudinal axis L-L from the bottom of the generally tubular stem portion 44 of about 1 inch to about 3 inches. This enables a user to grip the lower portion of the generally tubular stem portion 44 between the thumb and index finger below the location of the plurality of ridges 440.

The plurality of ridges 440 may be configured to provide feedback to a user in the same manner as described above with respect to the ridge 340 of the FIG. 9A sterilizable cover 310. The plurality of ridges 440 may be configured to provide a friction fit with a portion of the generally tubular grip portion 24 of the handle 20 in the same manner as described above with respect to the ridge 340 of the FIG. 9A sterilizable cover 310.

Like the ridge 340, the plurality of ridges 440 may be provided at any portion of the generally tubular stem portion 44 whether the lower generally tubular section 92 thereof as shown or the upper generally tubular section 90.

FIGS. 11A-11B show a sterilizable cover 510 in accordance with another embodiment of the invention. The FIG. 11A sterilizable cover 510 is in many respects similar to the above-described FIG. 1A, FIG. 8A, FIG. 9A, FIG. 10A sterilizable covers 10, 210, 310, 410 and consequently the same reference numerals are used to denote structures corresponding to similar structures in the sterilizable cover 510. In addition, the foregoing description of the FIG. 1A, FIG. 8A, FIG. 9A, FIG. 10A sterilizable covers 10, 210, 310, 410 is equally applicable to the FIG. 11A sterilizable cover 510 except as noted below. Moreover, it will be appreciated upon reading and understanding the specification that aspects of the sterilizable covers 10, 210, 310, 410, 510 may be substituted for one another or used in conjunction with one another where applicable.

Turning then to FIGS. 11A-11B, the generally tubular stem portion 44 of the sterilizable cover 510 includes a first inner surface 556 having a first textured surface 566 and a second inner surface 558 having a second textured surface 568 that is different from the first textured surface 566. The first and second textured surfaces 566, 568 may be formed by a texturing process, also known in the art as graining or engraving, wherein a pattern, that is a texture or grain, is added to the molding surface of a mold, which allows the mold to impress such pattern on the inner surface of the molded sterilizable cover 510. In the FIGS. 11A-11B embodiment, the first textured surface 566 has a first textured finish 576 and the second textured surface 568 has a second textured finish 578. The first textured finish 576 is relatively heavier than the second textured finish 578. In one form, the first textured finish may include a Mold Tech finish from a library of industry standard finishes for heavily textured finishes, for example, MT-11050 having a texture depth of 0.0045 inch and a draft angle of 6.5 degrees. The second textured finish 578 is relatively smoother and less textured than the first textured finish 576. In one form, the second textured finish 578 may include an SPI (Society of Plastics Industry) standard surface finish, for example, SPI B-1 having a surface roughness (roughness average RA) of 0.05 to 0.10 mm. The second textured finish 578 may include an optically clear finish, for example, at the distal end 52 of the generally tubular stem portion 44 to aid the afore described optically clear area 120 to pass camera imaging therethrough.

As shown in FIGS. 11A-11B, the first inner surface 556 may include at least a portion of an inner surface of the lower generally tubular section 92, for example, extending longitudinally from the top of the lower generally tubular section 92 linearly downward to just above the bend radius leading into the distal end 52 of the generally tubular stem portion 44. Further, as shown, at least a portion of the first inner surface 556 of the generally tubular stem portion 44 may form part of the friction fit portion 70. The second inner surface 558 may include an inner surface of the upper generally tubular section 90. Alternately, in some embodiments, the second inner surface 558 may include all inner surfaces of the sterilizable cover 10 other than the first inner surface 556.

The first and second textured surfaces 566, 568 of the sterilizable cover 510 enable the respective different first and second inner surfaces 556, 558 of the sterilizable cover 510 to provide their own distinct function. For example, the first textured surface 566 aids the friction fit between the friction fit portion 70 of the lower generally tubular section 92 and the handle grip portion 24 of the handle 20 upon receipt of the handle grip portion 24 in the cavity 60 of the generally tubular stem portion 44. The second textured surface 568, for example, aids in allowing a user to see the sterile control elements 80 covered by the sterilizable cover 510, see FIG. 5, and/or to enable better the passage of light though the second textured surface 568 from any covered illuminated components of the handle 20. The second textured surface 568, for example, as described above, may also aid the afore described optically clear area 120 to pass camera imaging through the distal end 52 of the generally tubular stem portion 44.

FIGS. 12A-12B show a sterilizable cover 610 in accordance with another embodiment of the invention. The FIG. 12A sterilizable cover 610 is in many respects similar to the above-described FIG. 1A, FIG. 8A, FIG. 9A, FIG. 10A, FIG. 11A sterilizable covers 10, 210, 310, 410, 510 and consequently the same reference numerals are used to denote structures corresponding to similar structures in the sterilizable cover 610. In addition, the foregoing description of the FIG. 1A, FIG. 8A, FIG. 9A, FIG. 10A, FIG. 11A sterilizable covers 10, 210, 310, 410, 510 is equally applicable to the FIG. 12A sterilizable cover 610 except as noted below. Moreover, it will be appreciated upon reading and understanding the specification that aspects of the sterilizable covers 10, 210, 310, 410, 510, 610 may be substituted for one another or used in conjunction with one another where applicable.

Turning then to FIGS. 12A-12B, the sterilizable cover 610 includes at least one ridge 340 projecting radially inward from the first inner surface 556 of the generally tubular stem portion 44. The ridge 340 is provided with the first textured surface 566 and the respective first textured finish 576. Alternately, the FIG. 12A sterilizable cover 610 may include a plurality of ridges 440 projecting radially inward from the first inner surface 556 of the generally tubular stem portion 44. The plurality of ridges 440 are provided with the first textured surface 566 and the respective first textured finish 576.

As will be appreciated from the foregoing description, the sterilizable covers 10, 210, 310, 410, 510, 610 being made of silicone rubber, have a flexible form factor and are highly customizable. Thus, for example, the sterilizable covers 10, 210, 310, 410, 510, 610 can be installed directly over existing integrated handle user interfaces for example that include control elements 80, as shown in FIGS. 5, 7A-7B, and 9C. Alternately, the sterilizable covers 10, 210, 310, 410, 510, 610 may be configured to be installed directly over integrated user interfaces of handles that incorporate a camera, for example as shown in FIGS. 8A-8B, where the integrated user interfaces may control attributes of the camera itself or other components of the system.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A sterilizable cover for a handle of an accessory of a medical suspended ceiling assembly, the handle having a generally tubular grip portion extending downward from a mounting structure of the accessory, the sterilizable cover comprising:
   a generally tubular stem portion having a sufficient size to be gripped by the human hand, wherein the stem portion has a proximal end that is open and a distal end that is closed, and defines a cavity along a longitudinal axis for receipt therein of the handle grip portion;
   wherein the generally tubular stem portion includes a friction fit portion that is configured to flex radially outwardly to create a friction fit with a portion of the handle grip portion upon receipt of the handle grip portion in the cavity of the generally tubular stem portion; and,
   an annular flange portion extending radially outwardly from the proximal end of the generally tubular stem portion;
   wherein the stem portion and the annular flange portion are a single continuous piece of flexible silicone rubber
   wherein the generally tubular stem portion has an upper generally tubular section protruding axially downward relative to the annular flange portion, a lower generally tubular section protruding axially downward relative to a bottom region of the upper generally tubular section, and a shoulder that transitions from the upper generally tubular section to the lower generally tubular section,
   wherein an inner perimeter of the upper generally tubular section is relatively wider in axial cross section than an inner perimeter of the lower generally tubular section, and
   wherein the upper generally tubular section, lower generally tubular section, and the shoulder are configured such that at least one of a squeeze force or a twist force about a longitudinal axis of the generally tubular stem portion applied to the upper generally tubular section causes an upper part of the shoulder to flex radially inwardly and, via force transfer through the shoulder, imparts a radially outward force to the lower generally tubular section including at the friction fit portion of the generally tubular stem portion to form a gap between the lower generally tubular section and the handle grip portion, thereby to loosen the friction fit therebetween, releasing the sterilizable cover from frictional engagement with the handle, enabling easy removal of the sterilizable cover from the handle.

2. The sterilizable cover of claim 1, wherein the generally tubular stem portion is tapered in a direction of the longitudinal axis from the proximal end to the distal end.

3. The sterilizable cover of claim 1, wherein at least a portion of the silicone rubber is translucent to enable the passage of light therethrough.

4. The sterilizable cover of claim 1, wherein the silicone rubber is configured to be steam sterilized in a pressurized autoclave, dry heat sterilized, or chemically sterilized, without degradation of the silicone rubber.

5. The sterilizable cover of claim 1, wherein the silicone rubber is configured to be resistant to temperatures between 70 and 570 degrees Fahrenheit.

6. The sterilizable cover of claim 1, wherein at least the distal end of the generally tubular stem portion has an optically clear area configured to enable camera imaging to pass therethrough.

7. The sterilizable cover of claim 1, wherein the generally tubular stem portion is circular in shape in axial cross section.

8. The sterilizable cover of claim 1, wherein the shoulder transitions radially inwardly from the inner perimeter of the upper generally tubular section to the inner perimeter of the lower generally tubular section.

9. The sterilizable cover of claim 1, wherein an inner perimeter of the upper generally tubular section is relatively wider in axial cross section than an outer perimeter of the lower generally tubular section.

10. The sterilizable cover of claim 1, wherein the sterilizable cover is stackable axially with respect to another sterilizable cover such that the lower generally tubular section of one sterilizable cover is nestable along at least a portion of the longitudinal axis within the cavity of the upper generally tubular section of another sterilizable cover.

11. The sterilizable cover of claim 10, wherein the upper generally tubular section of the other sterilizable cover is sized to receive the lower generally tubular section of the one sterilizable cover such that the bottom of the lower generally tubular section of the one sterilizable cover abuts a shoulder that transitions between the upper generally tubular section and the lower generally tubular section of the other sterilizable cover.

12. The sterilizable cover of claim 1, wherein the length of the upper generally tubular section along the longitudinal axis is in the range of 1 inch to 5 inches.

13. The sterilizable cover of claim 1, wherein the length of the lower generally tubular section along the longitudinal axis is in the range of 1 inch to 5 inches.

14. The sterilizable cover of claim 1, wherein the outer diameter of the upper generally tubular section is in the range of 1 inch to inches.

15. The sterilizable cover of claim 1, wherein the outer diameter of the lower generally tubular section is in the range of 0.5 inch to 3 inches.

16. The sterilizable cover of claim 1, wherein the lower generally tubular section includes one or more channels void of material on an inner surface of the lower generally tubular section in fluid communication with the cavity of the upper generally tubular section.

17. The sterilizable cover of claim 1, wherein the friction fit portion includes at least a portion of an inner surface of the generally tubular stem portion.

18. The sterilizable cover of claim 17, wherein the generally tubular stem portion has an upper generally tubular section protruding axially downward relative to the annular flange portion and a lower generally tubular section protruding axially downward relative to a bottom region of the upper generally tubular section, and the friction fit portion includes at least a portion of an inner surface of the lower generally tubular section.

19. The sterilizable cover of claim 1, comprising at least one ridge projecting radially inward from an inner surface of the generally tubular stem portion.

20. The sterilizable cover of claim 19, wherein the generally tubular stem portion has an upper generally tubular section protruding axially downward relative to the annular flange portion and a lower generally tubular section protruding axially downward relative to a bottom region of the upper generally tubular section, and further comprising at least one ridge projecting radially inward from an inner surface of the lower generally tubular section.

21. The sterilizable cover of claim 19, wherein the at least one ridge when seen in a direction along the longitudinal axis has a ring shape.

22. The sterilizable cover of claim 19, wherein the at least one ridge includes a plurality of ridges that when seen in a direction along the longitudinal axis form a discontinuous ring shape that is partly discontinuous.

23. The sterilizable cover of claim 19, wherein the at least one ridge projects radially inward from the inner surface to have a radially projecting width of about 0.01 inch to about 0.04 inch.

24. The sterilizable cover of claim 19, wherein the at least one ridge has a height along the longitudinal axis of about 0.02 inch to about 0.04 inch.

25. The sterilizable cover of claim 19, wherein the at least one ridge is located at a height along the longitudinal axis from the bottom of the generally tubular stem portion of about 1 inch to about 3 inches.

26. The sterilizable cover of claim 1, wherein a first inner surface of the generally tubular stem portion has a first textured surface, and a second inner surface of the generally tubular stem portion has a second textured surface that is different from the first textured surface.

27. The sterilizable cover of claim 26, wherein the first textured surface has a first textured finish and the second textured surface has a second textured finish, and the first textured finish is relatively heavier than the second textured finish.

28. The sterilizable cover of claim 27, wherein the second textured finish is relatively smoother and less textured than the first textured finish.

29. The sterilizable cover of claim 26, wherein the second textured finish includes an optically clear finish.

30. The sterilizable cover of claim 26, wherein at least a portion of the first inner surface of the generally tubular stem portion forms part of the friction fit portion.

31. The sterilizable cover of claim 26, wherein the generally tubular stem portion has an upper generally tubular section protruding axially downward relative to the annular flange portion and a lower generally tubular section protruding axially downward relative to a bottom region of the upper generally tubular section, wherein the second inner surface includes an inner surface of the upper generally tubular section.

32. The sterilizable cover of claim 31, wherein the first inner surface includes an inner surface of the lower generally tubular section.

33. The sterilizable cover of claim 26, comprising at least one ridge projecting radially inward from the first inner surface of the generally tubular stem portion.

34. The sterilizable cover of claim 1, wherein the wall thickness of the generally tubular stem portion is in the range of 0.04 inch to 0.16 inch.

35. The sterilizable cover of claim 1, wherein the silicone rubber has a Shore A hardness of 20 to 70.

* * * * *